United States Patent

De Lombaert et al.

Patent Number: 5,550,119
Date of Patent: Aug. 27, 1996

[54] PHOSPHONO SUBSTITUTED TETRAZOLE DERIVATIVES AS ECE INHIBITORS

[75] Inventors: Stéphane De Lombaert, Bernardsville; Arco Y. Jeng, Piscataway; Gary M. Ksander, Milford, all of N.J.

[73] Assignee: Ciba-Geigy Corporation, Tarrytown, N.Y.

[21] Appl. No.: 403,353

[22] Filed: Mar. 2, 1995

[51] Int. Cl.$^6$ ................................................. C07F 9/280
[52] U.S. Cl. ..................................................... 514/92
[58] Field of Search ................................................ 514/92

[56] References Cited

U.S. PATENT DOCUMENTS

| | | | |
|---|---|---|---|
| 5,155,100 | 10/1992 | Eriem et al. | 514/119 |
| 5,250,522 | 10/1993 | De Lambert | 514/114 |
| 5,273,990 | 12/1993 | De Lambert | 514/381 |
| 5,294,632 | 3/1994 | Erion et al. | 514/381 |

FOREIGN PATENT DOCUMENTS

| | | |
|---|---|---|
| 054862 | 11/1985 | European Pat. Off. |
| 618224 | 10/1994 | European Pat. Off. |
| 623625 | 11/1994 | European Pat. Off. |
| 141930 | 5/1980 | Germany . |
| 9311154 | 6/1993 | WIPO . |
| 9405677 | 3/1994 | WIPO . |
| 9428012 | 12/1994 | WIPO . |

OTHER PUBLICATIONS

CA 121:281220a Preparation . . . inhibitors. Erion et al., pp 1091, 1994.
Chem Abst. 117(7):70275b, Nachev, 1991.
K. Shiosaki et al. DN&P 7(10) Dec. 1994 pp.593–601.
T. Fukami et al. Biorganic & Medicinal Chem. letters vol. 4, No. 10 pp. 1257–1262 (1994).
S. De Lambert et al. Biochemical & Biophysical Research Comm. vol. 204, No. 1 (1994) Oct. 14, 1994.
B. Weiss et al. Res. Comm. in chemical Pathology & Pharmacology vol. 52, No. 1 Apr. 1986.
FASEB Journal Absts Endothelin/Endothelin Receptors, Mar. 15, 1994, A184.

Primary Examiner—Joseph K. McKane
Attorney, Agent, or Firm—Norbert Gruenfeld

[57] ABSTRACT

The present invention relates to the N-phosphonomethyl substituted compounds of formula

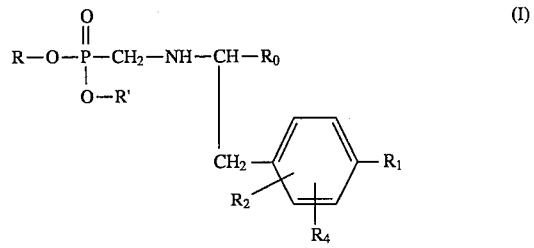

20 Claims, No Drawings

PHOSPHONO SUBSTITUTED TETRAZOLE DERIVATIVES AS ECE INHIBITORS

SUMMARY OF THE INVENTION

Endogenous atrial natriuretic peptides (ANP), also called atrial natriuretic factors (ANF) have diuretic, natriuretic and vasorelaxant functions in mammals. The natural ANF peptides are metabolically inactivated, in particular by a degrading enzyme which has been recognized to correspond to the enzyme neutral endopeptidase (NEP) EC 3.4. 24.11, also responsible for e.g. the metabolic inactivation of enkephalins.

The aim of the present invention is to provide novel phosphono substituted tetrazole derivatives described below which are useful as neutral endopeptidase (NEP) inhibitors, e.g. as inhibitors of the ANF-degrading enzyme in mammals, so as to prolong and potentiate the diuretic, natriuretic and vasodilator properties of ANF in mammals, by inhibiting the degradation thereof to less active metabolites. The compounds of the invention are thus particularly useful for the treatment of conditions and disorders responsive to the inhibition of neutral endopeptidase EC 3.4. 24.11, particularly cardiovascular disorders, such as hypertension, renal insufficiency including edema and salt retention, pulmonary edema and congestive heart failure. By virtue of their inhibition of neutral endopeptidase, the compounds of the invention may also be useful for the treatment of pain, depression and certain psychotic conditions. Other potential indications include the treatment of angina, premenstrual syndrome, Meniere's disease, hyperaldosteronism, hypercalciuria, ascites, glaucoma, asthma and gastrointestinal disorders such as diarrhea, irritable bowel syndrome and gastric hyperacidity.

Endothelin, a potent biological mediator in mammals, e.g. as a vasoconstrictor, is generated in mammals through enzymatic cleavage of the biologically inert big endothelin by endothelin-converting enzyme.

Surprisingly, the compounds of the invention inhibit the formation of endothelin, reduce the plasma and tissue levels of endothelin and inhibit the biological affects of endothelin activity in mammals. The compounds of the invention are thus of particular interest for the treatment of endothelin dependent conditions and diseases in which endothelin is a contributing factor, e.g. cardiovascular disorders such as essential hypertension, heart failure, pulmonary hypertension, cerebral ischemia, subarachnoid hemorrhage, renal failure, atherosclerosis, cerebral vasospasm, arterial hypertrophy, restenosis, arrhythmia and myocardial infarction, also respiratory disorders such as bronchial asthma, and gastrointestinal disorders such as inflammatory bowel disease or ischemic bowel disease, Crohn's disease, ulcerative colitis as well as endotoxic shock, preclampsia, diabetes, Raynand's disease, and the like.

DETAILED DESCRIPTION OF THE INVENTION

The present invention relates to the N-phosphonomethyl substituted tetrazole and amino acid derivatives of formula I

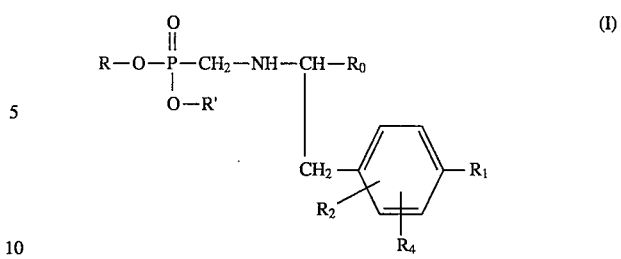

and tautomers thereof wherein
$R_0$ represents
(i) a group of formula

or
(ii) a group of formula —X—$COR_3$ (Ib);
R and R' represent independently hydrogen, carbocyclic aryl, 6-tetrahydronaphthyl, 5-indanyl, α-(trichloromethyl, carboxyl, esterified carboxyl or amidated carboxyl) substituted-(lower alkyl or aryl-lower alkyl), acyloxymethyl optionally monosubstituted on methyl carbon by lower alkyl, by $C_5$-$C_7$-cycloalkyl, by aryl or by aryl-lower alkyl; $R_1$ represents phenyl, or phenyl substituted by lower alkyl, lower alkoxy, halogen or trifluoromethyl; or $R_1$ represents thienyl or furanyl optionally substituted by lower alkyl; or $R_1$ represents hydrogen, if $R_0$ represents a group of formula Ia; $R_2$ and $R_4$ represent hydrogen, lower alkyl, hydroxy, lower alkoxy, halogen or trifluoromethyl; n is 0, 1 or 2; $COR_3$ carboxyl or carboxyl derivatized in form of a pharmaceutically acceptable ester; X represents a direct bond, $C_{1-4}$-alkylene or $C_{2-4}$-alkenylene; and pharmaceutically acceptable salts thereof; pharmaceutical compositions comprising said compounds; methods for preparation of said compounds and for the preparation of intermediates; and methods of treating disorders in mammals which are responsive to the inhibition of neutral endopeptidases by administration of said compounds to mammals in need of such treatment.

Compounds of formula I and derivatives thereof, depending on the nature of substituents, possess one or more asymmetric carbon atoms. The resulting diastereoisomers and optical antipodes are encompassed by the instant invention.

The tetrazoles can exist in tautomeric forms or mixtures thereof, in which the hydrogen can be located on any of the ring nitrogen: such are also encompassed by the instant invention.

Pharmaceutically acceptable ester derivatives are preferably prodrug derivatives, such being convertible by solvolysis or under physiological conditions to the free phosphono/carboxylic acids of formula I, e.g. the phosphonic acid esters illustrated in European Patent application No. 481,214 as prodrugs of phosphonate nucleotide analogs, and as described herein.

Examples of such phosphonic acid esters are aryl, tetrahydronaphthyl and indanyl esters; α-acyloxymethyl esters optionally substituted by lower alkyl, by $C_5$-$C_7$-cycloalkyl, by aryl or by aryl-lower alkyl; lower alkyl and aryl-lower alkyl esters, each substituted on the α-carbon by carboxy, esterified or amidated carboxy, or by trichloromethyl.

Preferred are the compounds of formula I and tautomers thereof wherein $R_0$ represents the group of the formula (Ia); n being zero, 1 or 2; R and R' independently represent hydrogen, carbocyclic aryl, α-(trichloromethyl, carboxyl, esterified carboxyl or amidated carboxyl) substituted-(lower alkyl or aryl-lower alkyl), (carbocyclic aroyloxy or lower-alkanoyloxy)methyl optionally substituted on the methyl carbon by lower-alkyl, by $C_5$-, $C_6$- or $C_7$-cycloalkyl or by carbocyclic aryl; $R_1$ represents phenyl or phenyl substituted by lower alkyl, lower alkoxy, halogen or trifluoromethyl; $R_2$ and $R_4$ represent hydrogen, lower alkyl, lower alkoxy, halogen or trifluoromethyl; and pharmaceutically acceptable salts thereof.

Particularly preferred are above said compounds of formula I and tautomers thereof wherein $R_0$ represents the group of the formula (Ia); n being zero, 1 or 2; R and R' independently represent hydrogen, lower-alkanoyloxymethyl or lower-alkanoyloxymethyl substituted on methyl by lower-alkyl, by cyclohexyl, by cyclopentyl or by phenyl.

Also particularly preferred are said compounds of formula I and tautomers thereof wherein $R_0$ represents the group of the formula (Ia); n being zero, 1 or 2; R and R' independently represent hydrogen, 5-indanyl, phenyl, or phenyl substituted by one, two or three substituents selected from lower alkyl, halogen, lower alkoxy, lower alkanoylamino, trifluoromethyl, lower alkyl-(thio, sulfinyl or sulfonyl), and lower alkoxycarbonyl.

Also particularly preferred are said compounds of formula I wherein $R_0$ represents the group of the formula (Ia); n being zero, 1 or 2; R and R' independently represent hydrogen or α-(carboxy, lower alkoxycarbonyl, carbocyclic arylmethoxycarbonyl, aminocarbonyl or mono- or di-lower alkylaminocarbonyl)-substituted-(lower alkyl or carbocyclic aryl-lower alkyl).

Particular embodiments of the invention relate to the compounds of formula I wherein $R_0$ represents the group of the formula (Ib); X represents a direct bond, alkylene grouping and an alkenylene grouping, respectively, as defined herein.

Preferred are the compounds of formula I wherein $R_0$ represents the group of the formula (Ib); X represents a direct bond, $C_{1-4}$-alkylene or $C_2$–$C_4$-alkenylene; R and R' independently represent hydrogen, carbocyclic aryl, α-(trichloromethyl, carboxyl, esterified carboxyl or amidated carboxyl) substituted-(lower alkyl or aryl-lower alkyl), (carbocyclic aroyloxy or $C_1$–$C_{20}$-alkanoyloxy)methyl optionally substituted on the methyl carbon by lower alkyl, by $C_5$-, $C_6$- or $C_7$-cycloalkyl or by carbocyclic aryl; $R_1$ represents phenyl or phenyl mono- or disubstituted by lower alkyl, lower alkoxy, halogen or trifluoromethyl; or $R_1$ represents thienyl or furanyl, each optionally substituted by lower alkyl; $R_2$ represents hydrogen; $COR_3$ represents carboxyl or carboxyl derivatized in form of a pharmaceutically acceptable ester; $R_4$ represents hydrogen, lower alkyl, lower alkoxy, halogen or trifluoromethyl; and pharmaceutically acceptable salts thereof.

Particularly preferred are above said compounds of formula I wherein $R_0$ represents the group of the formula (Ib); R and R' independently represent hydrogen, lower-alkanoyloxymethyl or lower-alkanoyloxymethyl substituted on methyl by lower alkyl, by cyclohexyl, by cyclopentyl or by phenyl.

Also particularly preferred are said compounds of formula I wherein $R_0$ represents the group of the formula (Ib); R and R' independently represent hydrogen, 5-indanyl, phenyl, or phenyl substituted by one, two or three substituents selected from lower alkyl, halogen, lower alkoxy, lower alkanoylamino, trifluoromethyl, lower alkyl-(thio, sufinyl or sulfonyl) and lower alkoxycarbonyl.

Also particularly preferred are said compounds of formula I wherein $R_0$ represents the group of the formula (Ib); R and R' independently represent hydrogen or α-(carboxy, lower alkoxycarbonyl, carbocyclic arylmethoxycarbonyl, aminocarbonyl, mono- or di-lower alkylaminocarbonyl or trichloromethyl) substituted-(lower alkyl or carbocyclic aryl-lower alkyl); and pharmaceutically acceptable salts thereof.

Advantageously, R and R' are either identical, or one of R and R' represents hydrogen while the other of R and R' has any of the other meanings as defined herein.

Also particularly preferred are the said compounds of formula I wherein $R_0$ represents the group of the formula (Ib); $COR_3$ represents carboxyl, lower alkoxycarbonyl, (carbocyclic or heterocyclic aryl)-lower alkoxycarbonyl, (di-lower alkylamino, N-lower alkylpiperazino, morpholino, pyrrolidino, piperidino or perhydrazepino)-$C_2$ to $C_4$-alkoxycarbonyl, dihydroxypropyloxycarbonyl protected in form of a ketal, 5-indanyloxycarbonyl, α-(lower alkoxycarbonyl or di-lower alkylaminocarbonyl)-lower alkoxycarbonyl or 1-(lower alkanoyloxy)-lower alkoxycarbonyl; and pharmaceutically acceptable salts thereof.

Advantageously, R and R' are either identical, or one of R and R' represents hydrogen while the other of R and R' has any of the other meanings as defined herein.

A particular embodiment of the invention relates to the compounds of formula II

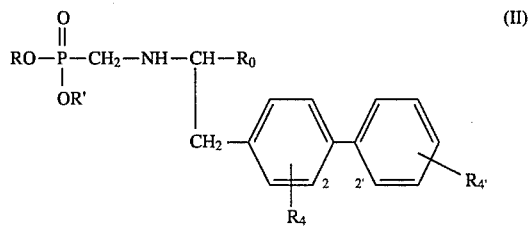

and tautomers thereof wherein $R_0$ represents a group of the formula (Ia) or (Ib); R and R' independently represent hydrogen, carbocyclic aryl, 5-indanyl, α-(carboxy, lower alkoxycarbonyl, carbocyclic arylmethoxycarbonyl, aminocarbonyl or mono- or di-lower alkylaminocarbonyl or trichloromethyl) substituted-(lower alkyl or carbocyclic aryl-lower alkyl), or

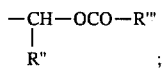

R" represents hydrogen, lower-alkyl, $C_5$-, $C_6$- or $C_7$-cycloalkyl or carbocyclic aryl; R''' represents lower-alkyl, $C_5$-, $C_6$- or $C_7$-cycloalkyl, carbocyclic aryl or carbocyclic aryl-lower alkyl; $COR_3$ represents carboxyl, $C_1$–$C_{20}$-alkoxycarbonyl, (carbocyclic or heterocyclic aryl)-lower alkoxycarbonyl, (di-lower alkylamino, N-lower alkylpiperazino, morpholino, pyrrolidino, piperidino or perhydrazepino)-$C_2$ to $C_4$-alkoxycarbonyl, dihydroxypropyloxycarbonyl protected in form of a ketal, 5-indanyloxycarbonyl, α-(lower alkoxycarbonyl or di-lower alkylaminocarbonyl)-lower alkoxycarbonyl; $R_4$ and $R_4'$ independently represent hydrogen, lower alkyl, lower alkoxy, halogen or trifluoromethyl; n is zero or 1; X represents a direct bond, $C_{1-2}$-alkylene or $C_2$-alkenylene; and pharmaceutically acceptable salts thereof.

Preferred are said compounds of formula II and tautomers thereof wherein $R_0$ represents a group of the formula (Ia); n being zero; $R_4$ and $R_4'$ independently represent hydrogen or lower alkoxy; and other symbols have meaning as defined above; and pharmaceutically acceptable salts thereof.

Preferred are said compounds of formula II wherein $R_0$ represents a group of the formula (Ib); $COR_3$ represents carboxyl; also preferred are said compounds wherein $R_4$ and $R_4'$ represent hydrogen or lower alkoxy; and other symbols have meaning as defined above; and pharmaceutically acceptable salts thereof.

Advantageously, R and R' are either identical, or one of R and R' represents hydrogen while the other of R and R' has any of the other meanings as defined herein.

A preferred embodiment of the invention relates to a compound of formula III

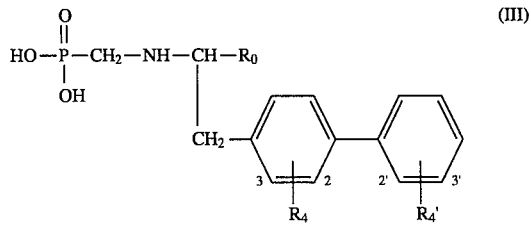

and tautomers thereof wherein $R_0$ represents a group of the formula (Ia) or (Ib); n being zero; $R_4$ and $R_4'$ represent hydrogen or $C_1$–$C_3$alkoxy; X represents a direct bond, methylene or ethenylene; and pharmaceutically acceptable mono-, di- or tri-ester derivatives thereof in which one, two or three of the acidic hydroxy groups of the carboxyl and phosphono functional groups are esterified in form of a mono-, di- or tri-pharmaceutically acceptable ester; pharmaceutically acceptable salts thereof; and optical or stereoisomers thereof.

The pharmaceutically acceptable ester derivatives thereof are preferably prodrug ester derivatives, such being convertible by solvolysis or under physiological conditions to the free acid of formula III.

Preferred embodiments are compounds of formulae IIIa and IIIb

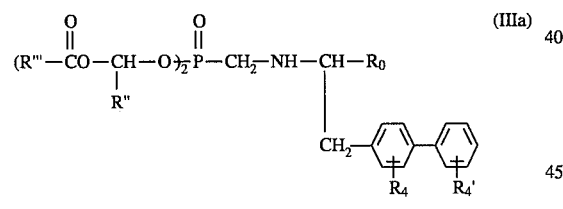

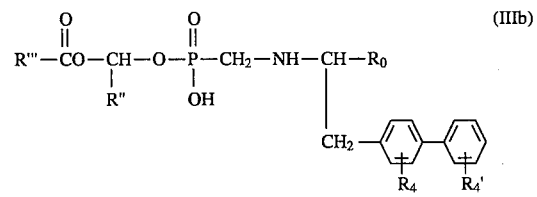

wherein $R_0$ represent the group of the formula (Ia) or (Ib); X represents a direct bond, methylene or ethenylene; n is zero; R" and R'" independently represent hydrogen, $C_1$–$C_{20}$-straight chain or branched alkyl, cyclohexyl, cyclopentyl or phenyl; $COR_3$ represents carboxyl; or $COR_3$ represents carboxyl esterified in form of a pharmaceutically acceptable prodrug ester preferably selected from $C_1$–$C_{20}$-alkoxycarbonyl, (carbocyclic or heterocyclic aryl)-methoxycarbonyl, (di-lower alkylamino)-$C_2$ to $C_4$-alkoxycarbonyl, dihydroxypropyloxycarbonyl protected in form of a ketal, (lower alkoxycarbonyl or di-lower alkylaminocarbonyl)-methoxycarbonyl, 5-indanyloxycarbonyl and 1-(lower alkanoyloxy)-lower alkoxycarbonyl; $R_4$ and $R_4'$ represent hydrogen or $C_1$–$C_3$alkoxy; and pharmaceutically acceptable salts thereof.

Preferred in turn are said compounds of formula IIIa wherein $R_0$ represent the group of the formula (Ia) or (Ib); R" and R'" have meaning as defined above and $COR_3$ represents carboxyl. Also preferred are said compounds of formula IIIb wherein $R_0$ represent the group of the formula (Ia) or (Ib); R" and R'" have meaning as defined above and $COR_3$ represents carboxyl.

Preferred esters are the compounds of formulae IIIc, IIId, IIIe and IIIf

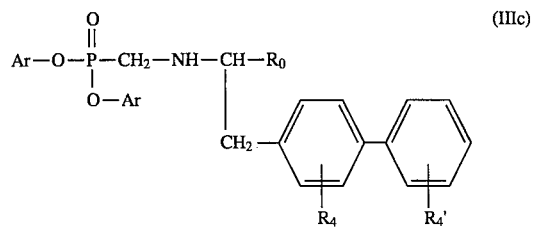

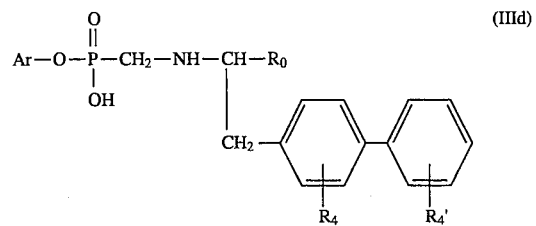

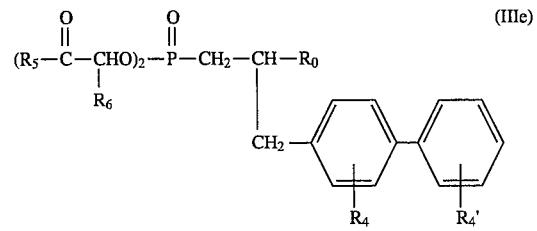

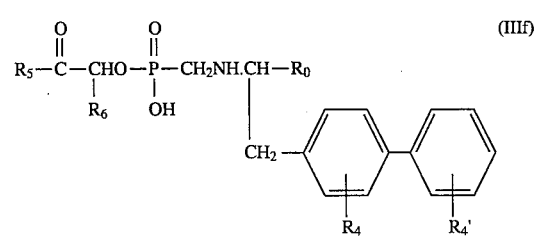

and tautomers thereof wherein $R_0$ represents a group of the formula (Ia) or (Ib); n being zero; Ar represents phenyl or phenyl substituted by lower alkyl, lower alkoxy, halogen, trifluoromethyl, lower alkanoylamino, lower alkyl-(thio, sulfinyl or sulfonyl) or lower alkoxycarbonyl; or Ar represents 5-indanyl; $R_5$ represents hydroxy, lower alkoxy, aryl-lower alkoxy or di-lower alkylamino; $R_6$ represents hydrogen or lower alkyl; $COR_3$ represents carboxyl; or $COR_3$ represents carboxyl esterified in form of a pharmaceutically acceptable prodrug ester preferably selected from $C_1$–$C_{20}$-alkoxycarbonyl, (carbocyclic or heterocyclic aryl)-methoxycarbonyl, (di-lower alkylamino)-$C_2$ to $C_4$-alkoxycarbonyl, dihydroxypropyloxycarbonyl protected in form of a ketal, (lower alkoxycarbonyl or di-lower alkylaminocarbonyl)-methoxycarbonyl, 5-indanyloxycarbonyl, 1-(lower alkanoyloxy)-lower alkoxycarbonyl; $R_4$ and $R_4'$ independently represent hydrogen or $C_1$–$C_3$alkoxy; X represents a direct bond, methylene or ethenylene; and pharmaceutically acceptable salts thereof.

A particular embodiment of the invention relates to compounds according to formulae II, III, IIIa, IIIb, IIIc, IIId, IIIe, and IIIf and tautomers thereof wherein $R_0$ represents a group of the formula (Ia) and $R_1$ is hydrogen, wherein the second ring of the biphenylyl ring is replaced by hydrogen (corresponding to formula I in which $R_1$ is hydrogen), and wherein the variables R and R' or R" and R'" or Ar or $R_5$ and $R_6$, respectively, and n and $R_4$ have the meanings given above in each case; and pharmaceutically acceptable salts thereof.

A particular embodiment of the invention relates to compounds according to formula IIIc and tautomers thereof wherein $R_0$ represents a group of the formula (Ia) or (Ib); n is zero; Ar represents phenyl or phenyl substituted by $C_1$–$C_4$alkyl, by $C_1$–$C_4$alkoxy, by lower alkanoylamino, by carboxy-methyl, by lower alkoxycarbonyl-methyl, by N,N-di-lower alkyl-aminocarbonyl-methyl, or by trichloromethyl; $COR_3$ represents carboxyl or $C_1$–$C_4$alkoxy-carbonyl; $R_4$ and $R_4'$ independently represent hydrogen or $C_1$–$C_3$alkoxy; X represents methylene, ethylene or ethenylene; and pharmaceutically acceptable salts thereof.

A particular embodiment of the invention relates to compounds according to formula IIIc and tautomers thereof wherein $R_0$ represents a group of the formula (Ia); n is zero; Ar represents phenyl or phenyl substituted by $C_1$–$C_4$alkyl; and $R_4$ and $R_4'$ independently represent hydrogen or $C_1$–$C_3$alkoxy; and pharmaceutically acceptable salts thereof.

Preferred in turn are corresponding compounds of formula IIIc, IIId, IIIe and IIIf wherein $COR_3$ represents carboxyl; and pharmaceutically acceptable salts thereof; also preferred are any of the above compounds wherein X is a direct bond.

A particular preferred embodiment of the invention relates to above compounds wherein n is zero having the (S)-configuration (at the asymmetric carbon bearing the tetrazole ring) [$R_0$=(Ia)].

A further particular embodiment of the invention relates to compounds having the configuration at the asymmetric center corresponding to (S)-biarylalanine [$R_0$=(Ib)].

Compounds of the invention, depending on the nature of substituents, can exist in the form of geometric isomers, racemates, diastereoisomers, pure enantiomers or mixtures thereof, all of which are within the scope of the invention.

The definitions used herein, unless denoted otherwise, have the following meanings within the scope of the present invention.

Carbocyclic aryl represents preferably monocyclic carbocyclic aryl or optionally substituted naphthyl.

Monocyclic carbocyclic aryl represents optionally substituted phenyl, being preferably phenyl or phenyl substituted by one to three substituents, such being advantageously lower alkyl, hydroxy, lower alkoxy, lower alkanoyloxy, halogen, cyano, trifluoromethyl, lower alkanoylamino, lower alkyl (thio, sulfinyl or sulfonyl) or lower alkoxycarbonyl.

Optionally substituted naphthyl represents 1- or 2-naphthyl or 1- or 2-naphthyl preferably substituted by lower alkyl, lower alkoxy or halogen.

Optionally substituted furanyl represents 2- or 3-furanyl or 2- or 3-furanyl preferably substituted by lower alkyl.

Optionally substituted thienyl represents 2- or 3-thienyl or 2- or 3-thienyl preferably substituted by lower alkyl.

Aryl as in aryl-lower alkyl is preferably phenyl or phenyl substituted by one or two of lower alkyl, lower alkoxy, hydroxy, lower alkanoyloxy, halogen, trifluoromethyl, cyano, lower alkanoylamino or lower alkoxycarbonyl.

Aryl-lower alkyl is advantageously benzyl or phenylethyl optionally substituted by one or two of lower alkyl, lower alkoxy, hydroxy, lower alkanoyloxy, halogen or trifluoromethyl.

The term "lower" referred to herein in connection with organic radicals or compounds respectively defines such with up to and including 7, preferably up and including 4 and advantageously one or two carbon atoms. Such may be straight chain or branched.

A lower alkyl group preferably contains 1–4 carbon atoms and represents for example ethyl, propyl, butyl or advantageously methyl.

A lower alkoxy group preferably contains 1–4 carbon atoms and represents for example methoxy, propoxy, isopropoxy or advantageously ethoxy.

The term $C_5$–$C_7$-cycloalkyl represents a saturated cyclic hydrocarbon radical which preferably contains 5 to 7 ring carbons and is, preferably cyclopentyl or cyclohexyl.

The term cycloalkyl(lower)alkyl represents preferably 1- or 2-(cyclopentyl or cyclohexyl)ethyl, 1-, 2- or 3-(cyclopentyl or cyclohexyl)propyl, or 1-, 2-, 3- or 4-(cyclopentyl or cyclohexyl)-butyl.

Esterified carboxy represents preferably lower alkoxycarbonyl, or aryl-lower alkoxycarbonyl.

Amidated carboxy represents preferably aminocarbonyl, mono- or di-lower alkylaminocarbonyl.

Amino-lower alkyl represents preferably amino-(ethyl, propyl or butyl), particularly omega-amino-(ethyl, propyl or butyl).

A di-lower alkylamino group preferably contains 1–4 carbon atoms in each lower alkyl portion and represents, for example, N,N-dimethylamino, N-methyl-N-ethylamino and advantageously N,N-diethylamino.

A lower alkoxycarbonyl group preferably contains 1 to 4 carbon atoms in the alkoxy portion and represents, for example, methoxycarbonyl, propoxycarbonyl, isopropoxycarbonyl or advantageously ethoxycarbonyl.

Lower alkoxycarbonyl-lower alkoxy represents advantageously e.g. 1-(ethoxycarbonyl)ethoxy or ethoxycarbonylmethoxy.

An aryl-lower alkoxycarbonyl group is preferably (monocyclic carbocyclic or heterocyclic)-substituted-lower alkoxy carbonyl, such as benzyloxycarbonyl.

Lower alkoxycarbonyl-lower alkoxy represents advantageously e.g. 1-(ethoxycarbonyl)ethoxy or ethoxycarbonylmethoxy.

Di(lower)alkylamino-lower alkoxy advantageously represents diethylaminoethoxy.

Halogen (halo) preferably represents fluoro or chloro, but may also be bromo or iodo.

Lower alkanoyl is preferably acetyl, propionyl, butyryl, or pivaloyl.

Lower alkanoyloxy is preferably acetoxy, pivaloyloxy or propionyloxy.

Acylamino represents preferably lower alkanoylamino, aroylamino, or aryl-lower alkoxycarbonylamino such as benzyloxycarbonylamino.

Lower alkanoylamino is preferably acetamido or propionamido.

Aroyl is preferably benzoyl or benzoyl substituted on the benzene ring by lower alkyl, lower alkoxy, halogen or trifluoromethyl.

Acyl represents preferably lower alkanoyl, carbocyclic aryl-lower alkanoyl, aroyl, lower alkoxycarbonyl or aryl-lower alkoxycarbonyl, advantageously lower alkanoyl. Lower alkoxycarbonyl for acyl is preferably t-butoxycarbonyl (abbreviated t-BOC). Aryl-lower alkoxycarbonyl for acyl is preferably benzyloxycarbonyl (abbreviated CBZ).

Lower alkylidene is preferably isopropylidene.

Cycloalkylidene is preferably cyclohexylidene.

Carboxyl esterified in form of a pharmaceutically acceptable ester represents advantageously a prodrug ester that may be convertible by solvolysis or under physiological conditions to the free carboxylic acid, such being preferably lower alkoxycarbonyl, advantageously lower alkoxycarbonyl; (amino, acylamino, mono- or di-lower alkylamino)-lower alkoxycarbonyl; carboxy-lower alkoxycarbonyl, e.g. alpha-carboxy-lower alkoxycarbonyl; lower alkoxycarbonyl-lower alkoxycarbonyl, e.g. alpha-lower alkoxycarbonyl-lower alkoxycarbonyl; α-(di-lower alkylamino, amino, mono-lower alkylamino, morpholino, piperidino, pyrrolidino, 1-lower alkylpiperazino)-carbonyl-lower alkoxycarbonyl; aryl-lower alkoxycarbonyl, preferably optionally (halo, lower alkyl or lower alkoxy)-substituted benzyloxycarbonyl, or pyridylmethoxycarbonyl; 1-(hydroxy, lower alkanoyloxy or lower alkoxy)-lower alkoxycarbonyl, e.g. pivaloyloxymethoxycarbonyl; (hydroxy, lower alkanoyloxy or lower alkoxy)-lower alkoxymethoxycarbonyl; bicycloalkoxycarbonyl-lower alkoxycarbonyl, e.g. bicyclo-[2,2,1]-heptyloxycarbonyl-lower alkoxycarbonyl, especially bicyclo-[2,2,1]-heptyloxycarbonylmethoxycarbonyl such as bornyloxycarbonylmethoxycarbonyl; 1-(lower alkoxycarbonyloxy)-lower alkoxycarbonyl; 5-indanyloxycarbonyl; 3-phthalidoxycarbonyl and (lower alkyl, lower alkoxy or halo)-substituted 3-phthalidoxycarbonyl; dihydroxypropyloxycarbonyl wherein hydroxy groups are free or are protected in the form of ketals, e.g. a lower alkylidene, a benzylidene or a 5- or 6-membered cycloalkylidene derivative, advantageously being (2,2-dimethyl-1,3-dioxolan-4-yl)-methoxycarbonyl.

Carboxyl esterified in form of a pharmaceutically acceptable prodrug ester represents most advantageously $C_1$–$C_4$-alkoxycarbonyl, benzyloxycarbonyl optionally substituted on phenyl by lower alkyl, lower alkoxy, halo or trifluoromethyl, 1-($C_2$–$C_4$-alkanoyloxy)-ethoxycarbonyl, (2,2-dimethyl-1,3-dioxolan-4-yl)-methoxycarbonyl, 5-indanyloxycarbonyl, 1-($C_1$–$C_4$-alkoxycarbonyloxy)-ethoxycarbonyl or 3-pyridylmethoxycarbonyl.

Esterified carboxyl as such represents advantageously lower alkoxycarbonyl or aryl-lower alkoxycarbonyl.

Amidated carboxyl represents advantageously aminocarbonyl, mono- or di-lower alkylaminocarbonyl.

Phosphono derivatized in the form of a pharmaceutically acceptable ester represents mono- or di-esters thereof, preferably phosphono derivatized as mono- or di-prodrug esters such as mono- or di-carbocyclic arylphosphono, e.g. mono- or di-phenylphosphono; mono- or di-5-indanylphosphono; mono- or di-acyloxymethylphosphono optionally substituted on methyl by lower-alkyl, by $C_5$–$C_7$-cycloalkyl, by aryl (e.g. phenyl) or by aryl-lower alkyl (e.g. benzyl), and wherein acyloxy represents lower-alkanoyloxy, $C_5$–$C_7$-cycloalkanoyloxy, carbocyclic aroyloxy or carbocyclic aryl-lower alkanoyloxy; as mono- or di-(α-lower alkoxycarbonyl-lower alkyl)phosphono; as mono- or di-(α-di-lower alkylaminocarbonyl-lower alkyl)phosphono; also as mono- or di-(α-trichloromethyl-lower alkyl)phosphono.

Phosphono derivatized as a mono- or di-prodrug ester relates to a pharmaceutically acceptable mono- or di-phosphono ester that may be convertible by solvolysis or under physiological conditions to phosphono (the free phosphonic acid).

Pharmaceutically acceptable salts are pharmaceutically acceptable acid addition salts for any basic compounds of the invention or salts derived from pharmaceutically acceptable bases for any acidic compounds of the invention.

Pharmaceutically acceptable salts of basic compounds of the invention are acid addition salts, which are preferably such of therapeutically acceptable inorganic or organic acids, such as strong mineral acids, for example hydrohalic, e.g. hydrochloric or hydro-bromic acid, sulfuric, phosphoric or nitric acid; aliphatic or aromatic carboxylic or sulfonic acids, e.g. formic, acetic, propionic, succinic, glycollic, lactic, malic, tartaric, gluconic, citric, maleic, fumaric, pyruvic, phenylacetic, benzoic, 4-aminobenzoic, anthranilic, 4-hydroxybenzoic, salicylic, 4-aminosalicylic, pamoic, nicotinic, methanesulfonic, ethanesulfonic, hydroxyethanesulfonic, 1,2-ethanedisulfonic acid, benzenesulfonic, p-toluenesulfonic, naphthalenesulfonic, sulfanilic, cyclohexylsulfamic acid, or ascorbic acid.

Pharmaceutically acceptable salts of the acidic compounds of the invention, e.g. those having a free phosphono hydroxyl group are salts formed with pharmaceutically acceptable bases, e.g. alkali metal salts (e.g. sodium, potassium salts), alkaline earth metal salts (e.g. magnesium, calcium salts), amine salts (e.g. ethanolamine, diethanolamine, triethanolamine, tromethamine salts).

The novel compounds of the invention are pharmacologically potent neutral endopeptidase enzyme inhibitors which inhibit e.g. the degradation of atrial natriuretic factors (ANF) in mammals. They thus potentiate the diuretic and natriuretic effect of exogenous or endogenous ANF in mammals.

The compounds of the invention are thus particularly useful in mammals as diuretic, natriuretic (saluretic) and antihypertensive agents for the treatment of e.g. hypertension, congestive heart failure and edema.

As neutral endopeptidase inhibitors, the compounds of the invention also inhibit enkephalinase so as to inhibit the degradation of endogenous enkephalins and may thus also be useful for the treatment of pain in mammals.

In addition, the compounds of the invention are pharmacologically active endothelin converting enzyme inhibitors which inhibit the formation of endothelin in mammals. They thus inhibit the biological effects of endothelin in mammals.

The compounds of the invention are thus also particularly useful in mammals e.g. for the treatment of e.g. cerebral ischemia, myocardial infarction and bronchial asthma.

The above-cited properties are demonstrable in vitro and in vivo tests, using advantageously mammals, e.g. mice, rats, dogs, monkeys or isolated organs, tissues, and mammalian, including human, enzymes thereof. Said compounds can be applied in vitro in the form of solutions, e.g. preferably aqueous solutions, and in vivo either enterally, parenterally, advantageously intravenously, e.g. as a suspension or in aqueous solution. The dosage in vitro may range between about $10^{-5}$ molar and $10^{-9}$ molar concentrations, more particularly between about $10^{-5}$ and $10^{-8}$ molar concentrations for endothelin converting enzyme inhibition. The dosage in vivo may range depending on the route of administration, between about 0.01 and 50 mg/kg, advantageously between about 1.0 and 25 mg/kg. For endothelin converting enzyme inhibition, the in vivo dosage may range between about 1 and 100 mg/Kg.

The analgesic activity can be determined by measuring the potentiation of the analgesic effects of enkephalin and derivatives thereof, and by classical analgesic tests, such as the phenyl-p-benzoquinone induced writing test [J. Pharmacol. Exp. Therap. 125, 237 (1959)] and the hot plate test in the mouse [J. Pharmacol. Exp. Therap. 107, 385 (1953).

The antihypertensive activity can be determined e.g. in the DOCA-salt hypertensive rat, and/or renal hypertensive rat or dog model.

The diuretic (saluretic) activity can be determined in standard diuretic screens, e.g. as described in "New Antihypertensive Drugs", Spectrum Publications, 1976, pages 307–321, or by measuring the potentiation of atrial natriuretic factor-induced natriuresis and diuresis in the rat.

The potentiation of ANF can also be determined by measuring the increase in ANF plasma level achieved.

The in vitro inhibition of neutral endopeptidase (NEP) 3.4.24.11 can be determined as follows:

The test compound is dissolved in dimethyl sulfoxide or 0.25M sodium bicarbonate solution, and the solution is diluted with pH 7.4 buffer to the desired concentration.

Neutral endopeptidase 3.4.24.11 activity is determined by the hydrolysis of the substrate glutaryl-Ala-Ala-Phe-2-naphthylamide (GAAP) using a modified procedure of Orlowski and Wilk (1981). The incubation mixture (total volume 125 µl) contains 4.2 µg of protein (rat kidney cortex membranes prepared by method of Maeda et al, 1983), 50 mM tris buffer, pH 7.4 at 25° C., 500 µM substrate (final concentration), and leucine aminopeptidase M (2.5 µg). The mixture is incubated for 10 minutes at 25° C. and 100 µl of fast garnet (250 µg fast garnet/ml of 10% Tween 20 in 1M sodium acetate, pH 4.2) is added. Enzyme activity is measured spectrophotometrically at 540 nm. One unit of NEP 24.11 activity is defined as 1 nmol of 2-naphthylamine released per minute at 25° C. at pH 7.4. $IC_{50}$ values are determined, i.e. the concentration of test compound required for 50% inhibition of the release of 2-naphthylamine.

Neutral endopeptidase activity can also be determined using ANF as a substrate. Atrial natriuretic factor degrading activity is determined by measuring the disappearance of rat-ANF (r-ANF) using a 3 minute reverse phase-HPLC separation. An aliquot of the enzyme in 50 mM Tris HCl buffer, pH 7.4, is preincubated at 37° C. for 2 minutes and the reaction is initiated by the addition of 4 nmol of r-ANF in a total volume of 50 µl. The reaction is terminated after 4 minutes with the addition of 30 µl of 0.27% trifluoroacetic acid (TFA). One unit of activity is defined as the hydrolysis of 1 nmol of r-ANF per minute at 37° C. at pH 7.4. $IC_{50}$ values are determined, i.e. the concentration of test compound required for 50% inhibition of the hydrolysis of ANF.

In vitro testing is most appropriate for the free phosphono/carboxylic acids of the invention.

Illustrative of the invention, (S)-[2-biphenyl-4-yl-1-(1H-tetrazol-5-yl)-ethylamino]-methylphosphonic acid demonstrates an $IC_{50}$ of about 1.6 nM in the GAAP in vitro assay.

Illustrative of the invention, (S)-2-(phosphonomethylamino)-3-(4-biphenylyl)-propionic acid demonstrates an $IC_{50}$ of about 15 nM in the GAAP in vitro assay.

The effect of the compounds of the invention on rat plasma ANF concentration can be determined as follows:

Male Sprague-Dawley rats (275–390 g) are anesthetized with ketamine (150 mg/kg)/acepromazine (10%) and instrumented with catheters in the femoral artery and vein to obtain blood samples and infuse ANF, respectively. The rats are tethered with a swivel system and are allowed to recover for 24 hours before being studied in the conscious, unrestrained state.

In this assay, plasma ANF levels are determined in the presence and absence of NEP inhibition. On the day of study, all rats are infused continuously with ANF at 450 ng/kg/min. i.v. for the entire 5 hours of the experiment. Sixty minutes after beginning the infusion, blood samples for baseline ANF measurements are obtained (time 0) and the rats are then randomly divided into groups treated with the test compound or vehicle. Additional blood samples are taken 30, 60, 120, 180 and 240 minutes after administration of the test compound.

Plasma concentrations are determined by a specific radioimmunoassay. The plasma is diluted (×12.5, ×25 and ×50) in buffer containing: 50 mM Tris (pH 6.8), 154 mM NaCl, 0.3% bovine serum albumin, 0.01% EDTA. One hundred microliters of standards [rANF (99–126)] or samples are added to 100 µl of rabbit anti-rANF serum and incubated at 4° C. for 16 hours. Ten thousand cpm of [$^{125}$I]rANF are then added to the reaction mixture which is incubated at 4° C. for an additional 24 hours. Goat anti-rabbit IgG serum coupled to paramagnetic particles is added to the reaction mixture and bound [$^{125}$I]rANF is pelleted by exposing the mixture to an attracting magnetic rack. The supenatant is decanted and the pellets counted in a gamma counter. All determinations are performed in duplicate. Plasma ANF levels are expressed as a percent of those measured in vehicle-treated animals which received ANF alone (450 ng/kg/min i.v.).

Illustrative of the invention, (S)-[2-biphenyl-4-yl-1-(1H-tetrazol-5-yl)-ethylamino]-methylphosphonic acid diphenyl ester at a dose of about 10 mg/kg p.o., administered in 10% ethanol/polyethylene glycol 400, produces significant increases in plasma ANF levels.

The antihypertensive effect can be determined in desoxycorticosterone acetate (DOCA)-salt hypertensive rats.

DOCA-salt hypertensive rats (280–380 g) are prepared by the standard method. Rats underwent a unilateral nephrectomy and one week later are implanted with silastic pellets containing 100 mg/kg of DOCA. The rats are maintained on 1% NaCl/0.2% KCl drinking water for three to five weeks until sustained hypertension is established. The antihypertensive activity is evaluated at this time.

Two days before an experiment, the rats are anesthetized with methoxyflurane and instrumented with catheters in the femoral artery to measure arterial blood pressure. Forty-eight hours later, baseline arterial pressure and heart rate are recorded during a 1 hour period. The test compound or vehicle is then administered and the same cardiovascular parameters are monitored for an additional 5 hours.

Illustrative of the invention, (S)-[2-biphenyl-4-yl-1-(1H-tetrazol-5-yl)-ethylamino]-methylphosphonic acid diphenyl ester at a dose of 10 mg/Kg p.o., administered in PEG 400, produces a significant reduction in blood pressure in the DOCA-salt hypertensive rat model.

The potentiation of the natriuretic effect of ANF can be determined as follows:

Male Sprague-Dawley rats (280–360 g) are anesthetized with Inactin (100 mg/kg i.p.) and instrumented with catheters in the femoral artery, femoral vein and urinary bladder to measure arterial pressure, administer ANF and collect urine, respectively. A continuous infusion of normal saline (33 ul/min) is maintained throughout the experiment to promote diuresis and sodium excretion. The experimental protocol consists of an initial 15 minute collection period (designated as pre-control) followed by three additional collection periods. Immediately after completion of the pre-control period, test compound or vehicle is administered; nothing is done for the next 45 minutes. Then, blood pressure and renal measurements are obtained during a second collection period (designated control; 15 min). At the conclusion of this period, ANF is administered (1 µg/kg i.v. bolus) to all animals and arterial pressure and renal parameters are determined during two consecutive 15 minutes collection periods.

Mean arterial pressure, urine flow and urinary sodium excretion are determined for all collection periods. Blood pressure is measured with a Gould p50 pressure transducer, urine flow is determined gravimetrically, sodium concentration is measured by flame photometry, and urinary sodium excretion is calculated as the product of urine flow and urine sodium concentration.

The in vitro inhibition of endothelin-converting enzyme can be determined as follows:

The test compound is dissolved in dimethyl sulfoxide or 0.25M sodium bicarbonate solution, and the solution is diluted with pH 7.4 buffer to the desired concentration.

Endothelin converting enzyme (ECE) is partially purified from porcine primary aortic endothelial cells by DE52 anion exchange column chromatrography and its activity is quantified by radioimmunoassay as described in Anal. Biochem. 213, 434–436 (1993). The ECE inhibition can be determined as described in Biochem. Mol. Biol. Int. 31, (5), 861–867 (1993), by radioimmunoassay to measure ET-1 formed from big ET-1.

Recombinant bovine ECE-1 has been described by Xu et al, Cell 78, 473 (1994). Human ECE has been described by Schmidt et al, Fed. Europ. Biochem. Soc. (FEBS) Letters 356, 238 (1994).

In vitro testing is most appropriate for the free phosphonic acids of the invention.

Illustrative of the invention, (S)-[2-biphenyl-4-yl-1-(1H-tetrazol-5-yl)-ethylamino]-methylphosphonic acid demonstrates an $IC_{50}$ of about 1.1 µM in the in vitro assay for porcine endothelin converting enzyme inhibition and an $IC_{50}$ of about 0.1µM for inhibition of human ECE (recombinant ECE-1 and ECE-2 obtained by tranfection of CHO cells with h-ECE-1 and h-ECE-2).

Endothelin converting enzyme inhibition can also be determined in vivo by measuring the inhibition of big ET-1-induced pressor response in the anesthesized rat. The effect of the inhibitors on the pressor response resulting from big ET-1 challenge is measured in Sprague-Dawley rats as described in Biochem. Mol. Biol. Int. 31, (5), 861–867 (1993). Results are expressed as percent inhibition of big ET-1-induced pressor response as compared to vehicle.

ECE inhibition can also be determined in vivo by measuring the inhibition big ET-1 induced pressor response in conscious spontaneously hypertensive rats (SHR), e.g. as described in Biochem. Biophys. Res. Communic. 204, 407–412 (1994).

Male SHR (16–18 weeks of age) are administered either test compound or vehicle (1M $NaHCO_3$) via an osmotic minipump implated subcutaneously. On day 5 femoral arterial and venous catheters are placed in anesthetized rats for the measurement of MAP (mean arterial pressure) and for test compound administration, respectively. After a 48 hour recovery period, MAP is recorded (day 7) through the arterial catheter connected to a pressure transducer. Blood pressure and heart rate are allowed to stabilize for 30 minutes before ganglion blockade is performed using chlorisondamine (10/kg i.v.). Approximately 15 minutes later, a bolus dose of big ET-1 (0.25 nmol/kg i.v.) is administered to both vehicle- and test compound treated rats. The change in blood pressure in response to big ET-1 is then compared between the two groups of rats at 1, 5, 10, 15, 30 and 60 min after dosing using a two-way ANOVA.

Bronchial effects can be determined by measuring the effect in a model of ET-1 induced bronchoconstriction.

Illustrative of the invention, continuous infusion of 5 mg/Kg/day of (S)-[2-biphenyl-4-yl-1-(1H-tetrazol-5-yl)-ethylamino]-methylphosphonic acid leads to a significant difference in reduction of big ET-1 induced pressor response in drug treated conscious spontaneous hypersensitive rats (as compared to those receiving vehicle control) over a period of 60 minutes.

Continuous infusion of 5 mg/Kg/day for 13 days of (S)-[2-biphenyl-4-yl-1-(1H-tetrazol-5-yl)-ethylamino]-methylphosphonic acid also produced a sustained reduction in the mean arterial pressure of spontaneous hypertensive rats (which were not administered exogenous big ET-1) using telemetry.

The effect on cerebral ischemia can be determined by measuring the effect on big ET-1 induced cerebral arterial contraction in the rabbit as described by P. Foley et al, Neurosurgery 34(1), 108–113 (1994).

The compounds of the invention are thus particularly useful as inhibitors of neutral endopeptidase, enhancing the potency and duration of action of atrial natriuretic peptide(s). The compounds are therefore particularly useful for the treatment of cardiovascular disorders such as hypertension, edema and salt retention, and cardiac conditions such as congestive heart failure. The invention furthermore relates to the use of the compounds according to the invention for the preparation of medicaments, in particular of medicaments useful for the treatment and prevention of cardiovascular disorders such as hypertension, edema and salt retention, and cardiac conditions such as congestive heart failure. Also included therein is the industrial preparation of the active substances in form of a commercial package.

The compounds of the invention which are also useful as endothelin converting enzyme inhibitors and as inhibitors of the endogenous formation of endothelin in mammals are of particular interest for the treatment of endothelin dependent disorders referred to herein. Illustrative thereof are cardiovascular conditions such as hypertension, renal failure, cardiac and cerebral ischemia, as well as respiratory disorders such as bronchial asthma.

The compounds of the invention can be prepared using processes described and illustrated below, e.g. by (a) reacting a compound of the formula

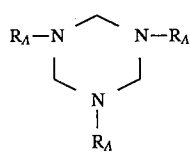
(IVa)

wherein $R_A$ represents

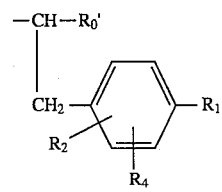
($R_A$)

wherein $R_0'$ represents
(i) a group of formula

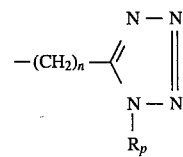
(Ic)

(ii) a group of formula —X—$COR_3$ (Ib); $R_1$, $R_2$, $R_4$, $COR_3$, X and n have meaning as defined hereinabove, and $R_p$ represents a protecting group; with disubstituted phosphite of the formula

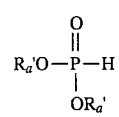
(IVb)

wherein $R_a$ and $R_a'$ have meaning as defined herein for R and R', except that $R_a$ and $R_a'$ do not represent hydrogen, and $R_a$ and $R_a'$ may in addition represent lower alkyl or aryl-lower alkyl; and removing the protecting group $R_p$ in resulting $R_p$ containing compounds; or reacting a said intermediate of formula IVa with tris(trimethylsilyl)phosphite, $P[OSi(CH_3)_3]_3$, in the presence of e.g. zinc chloride or $TiCl_4$ followed by an alcohol, e.g. methanol, to obtain a compound of formula I wherein R and R' represent hydrogen; or (b) condensing a compound of the formula Va

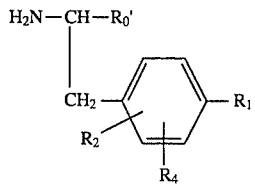
(Va)

wherein $R_0'$ represents a group of the formula (Ic) or (Ib), $R_1$, $R_2$, $R_4$ and n have meaning as defined hereinabove and $R_p$ is a protecting group; with a compound of the formula

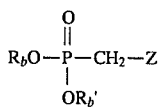
(Vb)

wherein $R_b$ and $R_b'$ represent lower alkyl or aryl-lower alkyl, e.g. optionally substituted benzyl, and Z represents a leaving group, e.g. a reactive esterified hydroxyl group, such as trifluoromethylsulfonyloxy; and removing the protecting group $R_p$ from corresponding resulting $R_p$ containing compounds; or, (c) for the manufacture of compounds of the formula I wherein $R_0$ represents the group of the formula (Ia), reacting an amide of the formula

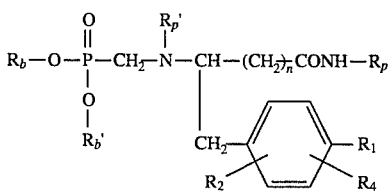
(VIa)

wherein $R_1$, $R_2$, $R_4$ and n have meaning as defined above; $R_b$ and $R_b'$ represent lower alkyl or aryl-lower alkyl, e.g. optionally substituted benzyl; and $R_p$ and $R_p'$ represent a protecting group;

with a di-lower alkyl azodicarboxylate and a triaryl phosphine (e.g. triphenylphosphine) and with hydrazoic acid (preferably generated in situ) or a reactive azide, such as trimethylsilyl azide, to obtain a compound of the formula

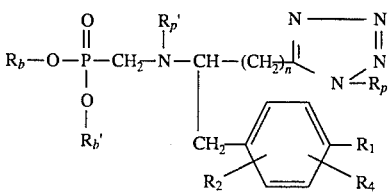
(VIb)

wherein $R_1$, $R_2$, $R_4$, n, $R_b$, $R_b'$, $R_p$ and $R_p'$ have meaning as defined above; and removing the protecting groups $R_p$ and $R_p'$; or, (d) for the manufacture of compounds of the formula I wherein $R_0$ represents the group of the formula (Ia), condensing a compound of the formula

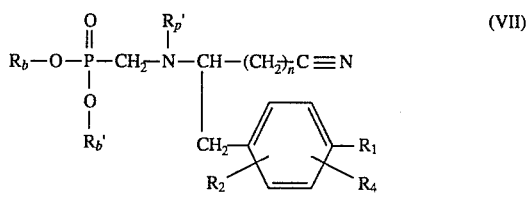
(VII)

wherein $R_1$, $R_2$, $R_4$, n, $R_p'$, $R_b$ and $R_b'$ have meaning as defined hereinabove, with hydrazoic acid (preferably generated in situ) or a reactive azide derivative, such as a trialkyl silyl azide or a trialkyltin azide, and liberating the free tetrazole from the resulting trialkylsilyl or trialkyltin substituted tetrazole by e.g. acid hydrolysis; and removing the protecting group $R_p'$; or, (e) for the manufacture of compounds of the formula I wherein $R_0$ represents the group of the formula (Ib), condensing under reductive amination conditions a compound of the formula VIIIa

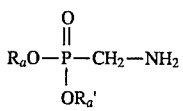
(VIIIa)

wherein $R_a$ and $R_a'$ have meaning as defined for R and R' in formula I, and $R_a$ and $R_a'$ may in addition represent lower alkyl or aryl-lower alkyl, with a compound of formula VIIIb

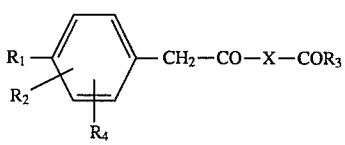
VIIIb wherein $R_1$, $R_2$, $R_4$, X and $COR_3$ have meaning as defined hereinabove;

(f) and converting any compound obtained in any said process, in which any of $R_a$, $R_b$, $R_a'$ and $R_b'$ represent lower alkyl or aryl-lower alkyl, to a corresponding product of the invention in which such have meaning as defined for R and R' in formula I; and in above said processes, if temporarily protecting any interfering reactive group(s), removing said protecting group(s), and then isolating the resulting compound of the invention; and, if desired, converting any resulting compound of the invention into another compound of the invention; and/or, if desired, converting a free phosphonic acid function into a pharmaceutically acceptable ester derivative, or converting a resulting ester into the free acid or into another ester derivative; and/or, if desired, converting a resulting free compound into a salt or a resulting salt into the free compound or into another salt, and/or, if desired, separating a mixture of isomers or racemates obtained into the single isomers or racemates, and/or, if desired, resolving a racemate into the optical antipodes.

In starting compounds and intermediates which are converted to the compounds of the invention in a manner described herein, functional groups present, such as phosphonyl, amino and hydroxy groups, are optionally protected by conventional protecting groups that are common in preparative organic chemistry. Protected phosphonyl, amino and hydroxy groups are those that can be converted under mild conditions into free phosphonyl, carboxyl, amino and hydroxy groups without other undesired side reactions taking place.

The purpose of introducing protecting groups is to protect the functional groups from undesired reactions with reaction components and under the conditions used for carrying out a desired chemical transformation. The need and choice of protecting groups for a particular reaction is known to those skilled in the art and depends on the nature of the functional group to be protected (phosphonyl, amino group, etc.), the structure and stability of the molecule of which the substituent is a part, and the reaction conditions.

Well-known protecting groups that meet these conditions and their introduction and removal are described, for example, in J. F. W. McOmie, "Protective Groups in Organic Chemistry", Plenum Press, London, New York 1973, T. W. Greene and P. G. M. Wuts, "Protective Groups in Organic Synthesis", Wiley, New York 1991, and also in "The Peptides", Vol. I, Schroeder and Luebke, Academic Press, London, New York, 1965.

Suitable protecting groups $R_p$ of protected 1H-tetrazol-5-yl are the protecting groups customarily used in tetrazole chemistry, especially triphenylmethyl, unsubstituted or substituted, for example nitro-substituted, benzyl, such as 4-nitrobenzyl, lower alkoxymethyl, such as methoxy- and ethoxy-methyl, also 1-ethoxyethyl, lower alkylthiomethyl, such as methylthiomethyl, silyl, such as tri-lower alkylsilyl, for example dimethyl-tert-butyl- and triisopropyl-silyl, and also 2-cyanoethyl, also lower alkoxy-lower alkoxymethyl, such as 2-methoxyethoxymethyl, benzyloxymethyl and phenacyl.

The removal of the protecting groups is carried out in accordance with known methods, for example as described in J. Green, Protective Groups in Organic Synthesis, Wiley-Interscience (1980). For example, the triphenylmethyl group is customarily removed by hydrolysis, especially in the presence of an acid, or by hydrogenolysis in the presence of a hydrogenation catalyst, 4-nitrobenzyl is removed, for example, by hydrogenolysis in the presence of a hydrogenation catalyst, methoxy- or ethoxy-methyl is removed, for example, by treatment with a tri-lower alkyl-, such as triethyl- or tributyl-tin bromide, methylthiomethyl is removed, for example, by treatment with trifluoroacetic acid, silyl radicals are removed, for example, by treatment with fluorides, such as tetra-lower alkylammonium fluorides, for example tetrabutylammonium fluoride, or alkali metal fluorides, for example sodium fluoride, 2-cyanoethyl is removed, for example, by hydrolysis, for example with sodium hydroxide solution, 2-methoxyethoxymethyl is removed, for example, by hydrolysis, for example with hydrochloric acid, and benzyloxymethyl and phenacyl are removed, for example, by hydrogenolysis in the presence of a hydrogenation catalyst.

A tetrazole protecting group $R_p$ is a group which can be introduced in form of an amide and such is e.g. cyanoethyl, p-nitrophenylethyl, lower alkoxycarbonylethyl, phenylsulfonylethyl and the like. Such tetrazole protecting groups can be removed by a retro-Michael deblocking reaction with a base such as DBN (1,5-diazabicyclo[4.3.0]non-5-ene), an amidine, an alkali metal carbonate or alkoxide, e.g. potassium carbonate, potassium t-butoxide, sodium methoxide in an inert solvent.

The amino protecting group $R_p'$ represents preferably on acyl protecting group such as t-butoxycarbonyl or benzyloxycarbonyl.

A reactive esterified hydroxyl group, such as Z in a compound of the formula Vb, IXe or XI, is a hydroxyl group esterified by a strong inorganic or organic acid. Corresponding Z groups are in particular halo, for example chloro, bromo or preferably iodo, also sulfonyloxy groups, such as lower alkyl- or arylsulfonyloxy groups, for example (methane-, ethane-, benzene- or toluene-) sulfonyloxy groups, also the trifluoromethylsulfonyloxy group.

The preparation of compounds of the invention according to process (a), i.e. the condensation of a hexahydrotriazine derivative of formula IVa with a phosphonic acid diester of formula IVb (the type of reaction is illustrated in U.S. Pat. No. 4,053,505 for the preparation of N-phosphonomethylglycine) is carried out in an inert solvent such as toluene or benzene, preferably at elevated temperature, to yield e.g. a compound of formula IVc

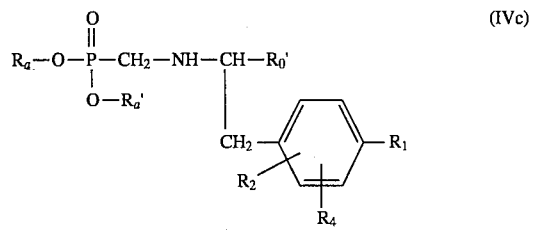

(IVc)

wherein R0', $R_1$, $R_2$, $R_4$, n, $R_p$, $R_a$ and $R_a'$ have meaning as defined above.

Condensation of a compound of formula IVa with tris(trimethylsilyl)phosphite can be carried out as known in the art for the type of reaction involved, e.g. as illustrated in Bull. Korean Chem. Soc. 1990, 11, 485 and Polish J. Chem. 1981, 55, 643.

Tris(trimethylsilyl)phosphite is commercially available or can be prepared as described in J. Am. Chem. Soc. 1974, 96, 7363.

The phosphonic acid (phosphite) diesters of formula IVb are known or can be prepared according to methods in the literature, e.g. U.S. Pat. No. 3,329,742 for the preparation of diaryl phosphites, by reaction of the alcohol corresponding to $R_a$ and $R_a'$ with phosphorus trichloride as illustrated herein.

Unsymmetrical phosphonic acid diesters can be prepared by first treating a symmetrical diester, e.g. dibenzyl phosphite, with aqueous base, e.g. aqueous tetramethyl ammonium hydroxide, to obtain a monoester, e.g. monobenzyl phosphite. This can be treated e.g. with an appropriate alkyl halide corresponding to R or R' in formula I, for example an α-alkoxycarbonylalkyl bromide, to obtain a compound of formula IVb wherein $R_a$ is benzyl and $R_a'$ is α-alkoxycarbonylalkyl. Alternatively, monobenzyl phosphite can first be converted to e.g. a mixed anhydride (e.g. with pivaloyl chloride) which is then reacted with an appropriate alcohol or phenol corresponding to R or R' in formula I to obtain a corresponding unsymmetrical diester of formula IVb. The resulting condensation product of formula IVc wherein either $R_a$ or $R_a'$ represents benzyl can then be converted to a compound of formula I wherein either R or R' represents hydrogen by selective catalytic hydrogenolysis of the benzyl substituent.

As to the hexahydrotriazines of formula IVa wherein $R_0'$ represents the group of the formula (Ic), such can be prepared from the N-acyl amino acid of the formula IXa

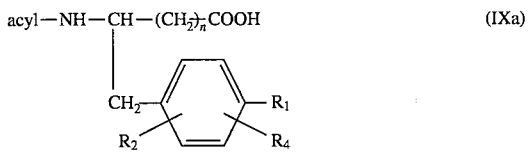

(IXa)

wherein $R_1$, $R_2$, $R_4$ and n have meaning as defined herein and acyl represents an easily removable acyl protecting group, as illustrated below.

For example, an N-acylbiarylalanine ester or chain length homologs thereof, e.g. N-t-butoxycarbonyl-4-biphenylalanine methyl ester, is selectively hydrolyzed with dilute base to the corresponding N-acylbiarylalanine, e.g. N-t-butoxycarbonyl-4-biphenylalanine. The carboxylic acid is converted e.g. to a mixed anhydride which is then treated with an amine of the formula IXb

wherein $R_p$ has meaning as defined herein, and the resulting amide is then treated under conditions of tetrazole formations, e.g. under conditions described in Tetrahedron Letters 1979, 491 and J. Org. Chem. 56 2395 (1991), such as by reaction with an azide such as trimethylsilyl azide upon amide activation, with e.g. diethyl azodicarboxylate and triphenylphosphine, to obtain a protected tetrazole intermediate which is then N-deacylated to the intermediate of formula Va

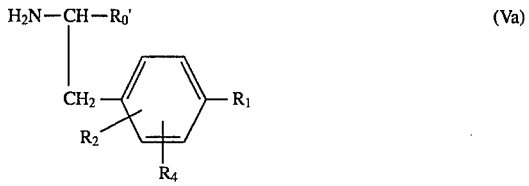

wherein $R_0'$, $R_1$ $R_2$, $R_4$ and $R_p$ have meaning as defined herein.

The hexahydrotriazines of formula IVa wherein $R_0'$ represents the group of formula Ib, e.g. when X is a direct bond, can be prepared as follows:

An N-acylbiarylalanine ester, e.g. N-t-butoxycarbonyl-4-biphenylalanine methyl ester, prepared as described herein, is selectively hydrolyzed with dilute base to the corresponding N-acylbiarylalanine, e.g. N-t-butoxycarbonyl-4-biphenylalanine. The carboxylic acid is converted to an ester of formula IXc

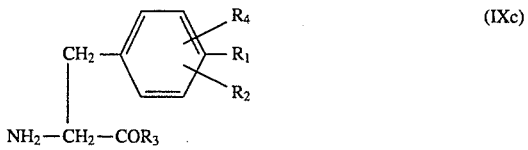

wherein $COR_3$ represents esterified carboxyl, and $R_1$, $R_2$ and $R_4$ have meaning as defined above.

Condensation of a tetrazole of formula Va wherein $R_0'$ represents the group of formula Ic, according to the general known process for the synthesis of hexahydrotriazine derivatives, e.g. as described in J. Org. Chem. 53, 3113 (1988), with formaldehyde, preferably 37% aqueous formaldehyde, advantageously in a solvent such as a mixture of ethyl acetate and water at room temperature, yields a corresponding hexahydrotriazine derivative of formula IVa.

The α-amino acid corresponding to starting materials of formula IXa (wherein n is zero) are either known in the art or can be prepared according to methods reported in the art. Such can be transformed into the next higher homologs according to procedures known in the art or methods described herein to obtain intermediates in which n is 1 or 2.

As to the preparation of the amino acid starting materials in optically active form, such can be prepared e.g. by resolution or by one of the following methods, as illustrated for biphenylalanines:

(1) Adapting a method described in J. Am. Chem. Soc. 1991, 113, 9276 a biarylmethanol, e.g. 4-biphenylylmethanol, is converted to a reactive derivative, e.g. the bromide, which is then condensed with an N-acyl derivative of 2,3-diphenyl-6-oxo-morpholine, e.g. the N-carbobenzyloxy-(2R,3S)-isomer, in the presence of a strong base such as sodium bis-trimethylsilylamide, to yield e.g. N-carbobenzyloxy-2(R),3(S),5(S)- 6-oxo-2,3-diphenyl-5-(4-biphenylylmethyl)-morpholine. Catalytic hydrogenolysis, e.g. using hydrogen and palladium on charcoal as catalyst, yields the optically active (S)-(+)-4-biphenylalanine.

(2) Alternatively, using the Pd (0)-catalyzed cross-coupling reaction described by W. Shieh et al, J. Organic Chemistry, 57, 379 (1992) the substantially optically pure chiral biarylalanines, of the formula

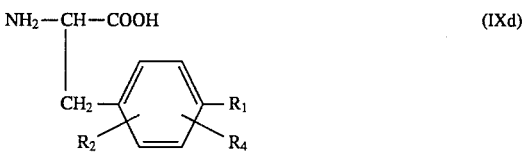

or the N-acyl and/or carboxy ester derivatives thereof wherein $R_1$ represents aryl and $R_2$ and $R_4$ have meaning as defined hereinabove, can be prepared by: condensing a reactive esterified optically active tyrosine derivative of the formula

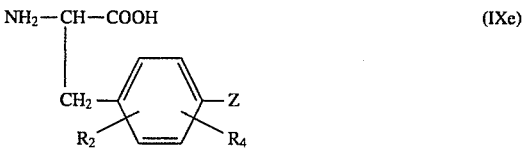

wherein the amino and carboxy groups are in protected form (as N-acyl and esterified carboxy ester derivatives), and Z represents reactive esterified hydroxy (advantageously trifluoromethylsulfonyloxy) with an aryl boronic acid in which aryl corresponds to $R_1$ as defined above, in the presence of a palladium (0) catalyst, in particular tetrakis(triphenylphosphine)palladium (0), and in the presence of an anhydrous base (such as an alkali metal carbonate), in an inert solvent (such as xylene or toluene) at an elevated temperature ranging from about 50° to 150° C., and removing any protecting groups as required.

For example, N-t-butoxycarbonyl-tyrosine methyl ester is first converted to N-t-butoxycarbonyl-4-trifluoromethylsulfonyloxy-phenylalanine methyl ester (N-t-butoxycarbonyl-tyrosine triflate methyl ester). This compound is then condensed with an arylboronic acid (e.g. phenylboronic acid) in the presence of anhydrous potassium carbonate, and tetrakis (triphenylphosphine) palladium (0) complex as catalyst, in toluene preferably at an elevated temperature, advantageously at about 100° to obtain N-t-butoxycarbonyl-4-biphenylalanine methyl ester. After N-deacylation, substantially optically pure 4-biphenylalanine methyl ester is obtained with a configuration corresponding to that of the tyrosine derivative used as starting material.

The arylboronic acids are either commercial or can be prepared as described in the literature, e.g. J. Org. Chem. 49, 5237 (1984).

The preparation of the compounds of the invention according to process (b) involves the condensation of a compound of formula Va, with a reactive esterified derivative of hydroxymethylphosphonic acid of formula Vb, e.g. dimethyl (trifluoromethylsulfonyloxy)-methylphosphonate (prepared e.g. according to Organic Synthesis 64, 80 (1985) and Tetrahedron Letters 1986, 1477) in a polar solvent, such as methylene chloride, in the presence of a base, e.g. a tertiary amine such as diisopropylethylamine, at a temperature near room temperature. The resulting protected tetrazoles can be selectively deprotected to the free tetrazoles with a base, e.g. DBU in an inert solvent, such as methylene chloride. The resulting carboxylic acid ester can be selectively hydrolyzed to the carboxylic acid according to methods for carboxylic acid ester hydrolysis well known in the art.

The biarylalanine starting materials (when X is a direct bond) are either known in the art or can be prepared according to methods reported in the art.

Such can be transformed into the next higher homologs according to procedures known in the art or methods described herein.

For example, N-t-butoxycarbonyl-4-biphenylalanine is converted to a mixed anhydride which is treated with diazomethane followed by rearrangement of the resulting diazoketone with e.g. silver benzoate and methanol to obtain 3-(t-butoxycarbonylamino)-4-(biphenyl-4-yl)butyric acid methyl ester.

As to the starting materials wherein X represents alkenylene, such can also be prepared from the corresponding N-protected biarylalanines. For example N-t-butoxycarbonyl-4-biphenylalanine, derivatized as a mixed anhydride, is reduced to the corresponding alcohol (e.g. with sodium borohydride) which is in turn oxidized to the aldehyde (e.g. by Swern oxidation with dimethylsufoxide and triethylamine). A Wittig type condensation with e.g. (carboethoxymethylene)triphenylphosphorane yields the N-protected starting material of formula VIa wherein $R_1$ is phenyl, $R_2$ and $R_4$ are hydrogen and X is —CH=CH—.

The preparation of the compounds of the invention according to process (c) can be carried out according to methodology for tetrazole ring formation as described under process (a) above for the preparation of tetrazole intermediates of formula Va.

The starting amides of formula VIa can be prepared by condensation of the respective carboxylic acids or esters with an amine of formula IXb.

The carboxylic acids can in turn be obtained from esters thereof which can be prepared according to process (a) above from compounds of formula IVa wherein $R_0'$ represents a group of formula (Ib) wherein $COR_3$ represents esterified carboxyl.

Alternately, the carboxylic acids can be prepared by condensing under reductive amination conditions a compound of the formula Xa

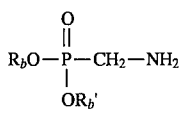

(Xa)

wherein $R_b$ and $R_b'$ represent lower alkyl or aryl-lower alkyl, with a compound of formula Xb

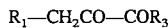 (Xb)

wherein $R_1$ has meaning as defined hereinabove, and $COR_3$ represents esterified carboxyl, such as lower alkoxycarbonyl.

The preparation involves the reductive amination of the appropriate pyruvic acid or derivative thereof of formula Xb with a diester of aminomethylphosphonic acid of formula Xa (e.g. the dimethyl ester), in the presence of a reducing agent such as hydrogen or sodium cyanoborohydride under standard reductive amination conditions, e.g. as illustrated in the examples to obtain compounds of formula Xc

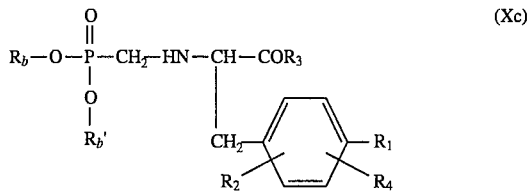

wherein $R_1$, $R_b$, and $R_b'$ have meaning as defined above, and $COR_3$ represents esterified carboxy.

The aminomethylphosphonic acid diesters of formula Xa are prepared according to methods known in the art, for instance by reaction of phthalimidomethyl bromide with trimethylphosphite [$P(OCH_3)_3$] to obtain the corresponding dimethyl phthalimidomethyl phosphonate which is converted with hydrazine to dimethyl aminomethylphosphonate.

As to the pyruvic acid esters of formula Xb, such are known in the art or are in turn prepared by methods analogous to those used for the preparation of substituted pyruvic acids, e.g. by condensation of e.g. the methyl ester of a biarylacetic acid with diethyl oxalate in the presence of a base, e.g. potassium t-butoxide, followed by hydrolyric decarboxylation.

The preparation of the compounds of the invention according to process (d) can be carried out according to procedures known in the art for the preparation of tetrazoles from nitriles e.g. as described in J. Am. Chem. Soc. 80, 3908 (1958) and J. Org. Chem. 56, 2395 (1991).

Hydrazoic acid is preferably generated from ammonium chloride/sodium azide in situ.

The starting nitriles can be prepared in a conventional manner from the corresponding primary amides which can in turn be obtained from the carboxylic acid esters, described under process (c), by treatment with ammonia.

If a trialkylsilyl azide (such trimethylsilyl azide) or a trialkyltin azide is used, the resulting tetrazole may be substituted by trialkyltin or trialkylsilyl. Such groups may be removed by hydrolysis, e.g. dilute acid.

The preparation of compounds of the invention according to process (e) under conditions of reductive amination, involves the reductive amination of the appropriate keto acid or derivative thereof of formula VIIIb with a diester of aminomethylphosphonic acid of formula VIIIa (e.g. the dimethyl ester), in the presence of a reducing agent such as hydrogen or sodium cyanoborohydride under standard reductive amination conditions, e.g. as illustrated in the examples to obtain compounds of the formula Xd

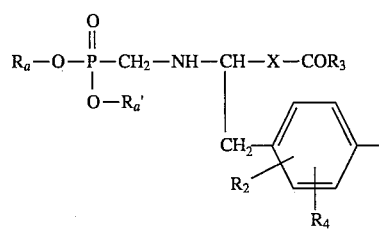

wherein $R_1$, $R_2$, $R_4$, $R_a$, $R_a'$ and $COR_3$ have meaning as defined above.

The aminomethylphosphonic acid diesters of formula VIIIa are prepared according to methods known in the art, for instance by reaction of phthalimidomethyl bromide with trimethylphosphite [$P(OCH_3)_3$] to obtain the corresponding dimethyl phthalimidomethyl phosphonate which is converted with hydrazine to dimethyl aminomethylphosphonate.

As to the keto acids of formula VIIIb such are known in the art or are e.g. in turn prepared by methods analogous to those used for the preparation of substituted pyruvic acids, when X is a direct bond, by condensation of e.g. the methyl ester of a biarylacetic acid with diethyl oxalate in the presence of a base, e.g. potassium t-butoxide, followed by hydrolytic decarboxylation.

The conversion according to process (f) of products obtained in the above processes, e.g. of formula IVc and Xc wherein $R_a$, $R_a'$, $R_b$ and $R_b'$, represent lower alkyl or aryl-lower alkyl to compounds of formula I can be carried out using known reagents for converting phosphonic acid esters to phosphonic acids, e.g. hydrobromic acid in glacial acetic acid, trimethylsilyl bromide, or by catalytic hydrogenation when such represent optionally substituted benzyl.

The compounds of the invention so obtained, can be converted into each other according to conventional methods. Thus, for example, resulting carboxylic acid esters may be hydrolyzed with aqueous alkalies, such as alkali metal carbonates or hydroxides. Resulting free acids may be esterified with e.g. unsubstituted or substituted alkanols corresponding to $R_3$ or reactive esterified derivatives thereof such as alkyl halides, or diazoalkanes. Free acids are also converted into said metal, ammonium or acid addition salts in conventional manner. Thus, any resulting free acid can be converted into a corresponding metal, ammonium or acid addition salt respectively, by reacting it with an equivalent amount of the corresponding base, e.g. said free acids with alkali or ammonium hydroxides or carbonates. Any resulting salt may also be converted into the free compound, by liberating the latter with stronger acids. In view of the close relationship between the free compounds and the salts thereof, whenever a compound of the invention, or intermediate, is referred to in this context, a corresponding salt is also intended, provided such is possible or appropriate under the circumstances.

The compounds, including their salts, may also be obtained in the form of their hydrates, or include other solvents used for the crystallization.

Furthermore, the functional derivatives of the free acids of formula I, wherein the phosphono hydroxyl groups are esterified by identical or different radicals may be prepared by condensing a free phosphonic acid of formula I or a mono-ester derivative thereof with an esterifying agent of the formula XI

$$R_7\text{—}Z \quad (XI)$$

wherein Z represents hydroxy or a reactive esterified hydroxyl group; and $R_7$ represents an esterifying radical as defined herein for the phosphonyl esters (e.g. R and R') and the carboxylic esters (encompassed e.g. by $COR_3$ representing esterified carboxy), in particular said non-aromatic radicals.

A reactive esterified hydroxyl group, such as Z in a compound of the formula Vb, IXe or XI, is a hydroxyl group esterified by a strong inorganic or organic acid. Corresponding Z groups are in particular halo, for example chloro, bromo or preferably iodo, also sulfonyloxy groups, such as lower alkyl- or arylsulfonyloxy groups, for example (methane-, ethane-, benzene- or toluene-) sulfonyloxy groups, also the trifluoromethylsulfonyloxy group.

The esterification of the carboxyl or phosphonyl groups, optionally in salt form, with a compound of formula XI wherein Z represents a reactive esterified hydroxyl group, is performed in a manner known per se, in the presence of for example an organic base, such as an organic amine, for example a tertiary amine, such as tri-lower alkylamine, for example trimethylamine, triethylamine or ethyl-di-isopropylamine, an N,N-di-lower-alkyl-aniline, for example N,N-di-methylaniline, a cyclic tertiary amine, such as an N-lower-alkylated morpholine, for example N-methyl-morpholine, a base of the pyridine type, for example pyridine, an inorganic base, for example hydroxides, carbonates, or hydrogen carbonates of alkali metals or alkaline-earth metals, for example sodium, potassium or calcium hydroxide, carbonate or hydrogen carbonate, or a quaternary ammonium base, such as a tetraalkylammonium hydroxide, carbonate or hydrogen carbonate, for example in which alkyl is e.g. methyl, ethyl, propyl, isopropyl, butyl, or the like, or an alkali metal salt of bis-trialkylsilylamide (e.g. trimethyl) optionally in the presence of a crown ether such as 18-crown-6 in a suitable inert solvent or solvent mixture, e.g. acetonitrile, toluene, and the like.

A trifunctional free acid, e.g. of the formula I, or a monoester or diester thereof, is preferably first converted into a salt of one of the stated organic or inorganic bases, especially into the sodium or potassium salt, and is then reacted with a compound of the formula XI. The compounds of formula XI are known or can be prepared by methods well-known to the art.

A compound of the formula XI wherein Z is a reactive esterified hydroxyl group can be prepared in situ. For example, a compound of the formula XI wherein Z is chloro can be converted by treatment with sodium iodide in a solvent, for example in acetone or acetonitrile, into a compound of the formula XI wherein Z is iodo; or esterification can be carried out with a chloro compound of the formula XI in the presence of sodium iodide.

Esterification of a compound with a free carboxyl group using in excess an alcohol of formula XI (wherein Z represents hydroxy) is carried out in a manner known per se, e.g. in the presence of an acid catalyst e.g. sulfuric acid or boron trifluoride etherate, preferably at an elevated temperature, advantageously ranging from about 40° C. to 100° C. Alternately, the esterification of a compound with a free carboxyl group can be carried out with at least an equimolar amount of the alcohol in the presence of a condensing agent such as dicyclohexylcarbodiimide or N-(3-dimethylaminopropyl)-N'-ethylcarbodiimide in a polar solvent such as methylene chloride, in the presence of a base if required, e.g. such as 4-(dimethylamino)pyridine.

Conversely, esters of the invention, phosphonic acid or carboxylic acid esters, can be converted to compounds of the invention with a free carboxy and/or one or two free phosphonyl hydroxy groups using methods and conditions generally known in the art and illustrated herein. Depending on type of ester involved, useful reagents include aqueous acids or bases; also anhydrous reagents such as trialkylsilyl halides, hydrobromic acid in glacial acetic acid; also hydrogen and a hydrogenolysis catalyst. For instance, trialkyl esters can be converted to the free trifunctional acids by treatment with hydrobromic acid in glacial acetic acid, e.g. at room temperature or elevated temperature. Also trialkyl esters can be converted to the mono esters wherein carboxy only remains esterified, by treatment with e.g. trimethylsilyl bromide at room temperature.

Esters of the invention (phosphonic acid di-esters), can be converted to compounds of the invention with one or two free phosphonyl hydroxy groups using methods and conditions generally known in the art and illustrated herein. Depending on type of ester involved, useful reagents include aqueous acids or bases; also anhydrous reagents such as trialkylsilyl halides, hydrobromic acid in glacial acetic acid; also hydrogen and a hydrogenolysis catalyst. For instance, dialkyl esters can be converted to the free phosphonic acids by treatment with hydrobromic acid in glacial acetic acid, e.g. at room temperature or elevated temperature.

Any benzyl esters can be selectively hydrogenolyzed with e.g. hydrogen in the presence of a catalyst such as palladium on charcoal.

Phosphono diesters wherein the esterifying groups (R and R') represent α-acyloxyalkyl can be converted to corresponding phosphono monoesters (wherein one of R and R' represents hydrogen) by treatment with one molar equivalent of an aqueous base, e.g. 1N sodium hydroxide.

Phosphono diesters wherein the esterifying groups (e.g. R and R' in formula I) represent aryl (for instance the compounds of formula IIIc) can advantageously be converted to the corresponding phosphono monoesters (wherein one of R and R' represents hydrogen) using dilute aqueous acid (e.g. dilute hydrochloric acid) in a polar water miscible solvent such as acetonitrile.

Furthermore, phosphono diesters wherein the esterifying groups represent aryl can first be converted to the corresponding phosphono diesters wherein the esterifying groups represent e.g. methyl, by treatment with methanol in the presence of potassium fluoride and a crown ether such as 18-crown-6. Subsequent treatment with hydrobromic acid in glacial acetic acid yields the free phosphonic acid.

In the case mixtures of stereoisomers or optical isomers of the above compounds are obtained, these can be separated into the single isomers by methods in themselves known, e.g., by fractional distillation, crystallization and/or chromatography. Racemic products can be resolved into the optical antipodes, for example, by separation of diastereomeric salts thereof, e.g., for basic compounds by the fractional crystallization of d- or l-(tartrate, mandelate or camphorsulfonate) salts, or for acidic compounds by fractional crystallization of d- or l-(alpha-methylbenzylamine, cinchonidine, cinchonine, quinine, quinidine, ephedrine, dehydroabietylamine, brucine or strychnine)-salts.

The above-mentioned reactions are carried out according to standard methods, in the presence or absence of diluents, preferably such as are inert to the reagents and are solvents thereof, of catalysts, alkaline or acidic condensing or said other agents respectively and/or inert atmospheres, at low temperatures, room temperature or elevated temperatures, preferably near the boiling point of the solvents used, at atmospheric or superatmospheric pressure.

The present invention relates also to novel starting materials that have been developed specifically for the manufacture of the compounds according to the invention, especially the selection of starting materials resulting in the final compounds referred to at the beginning as being preferred, wherein the variables have the meanings as indicated, to processes for the manufacture thereof, and to the use as intermediates.

The invention further includes any variant of said processes, in which an intermediate product obtainable at any stage of the process is used as a starting material and any remaining steps are carried out, or the process is discontinued at any stage thereof, or in which the starting materials are formed under the reaction conditions, or in which the reaction components are used in the form of their salts or optically pure antipodes. Mainly those starting materials should be used in said reactions, that lead to the formation of those compounds indicated above as being preferred.

The invention relates especially to the processes described in the Examples.

The present invention additionally relates to the use in mammals of the compounds of the invention and their pharmaceutically acceptable, non-toxic acid addition salts, or pharmaceutical compositions thereof, as medicaments, e.g. as neutral endopeptidase inhibitors, e.g. for the treatment of cardiovascular disorders such as hypertension, edema, salt retention and congestive heart failure.

The invention further relates to the use in mammals of the compounds of the invention as endothelin converting enzyme inhibitors so as to reduce the endogenous formation of endothelin and reduce the level of endogenous endothelin. The compounds can thus be used for the treatment of endothelin dependent disorders referred to hereinabove, such as endothelin dependent hypertension, cardiac and cerebral ischemia, endothelin dependent bronchial asthma, and endothelin dependent renal failure.

The present invention also relates to the use of the compounds of the invention for the preparation of pharmaceutical compositions especially pharmaceutical compositions having neutral endopeptidase inhibiting activity, and e.g. antihypertensive or saluretic activity.

The present invention additionally relates to the use of the compounds of the invention for the preparation of pharmaceutical compositions having endothelin converting enzyme inhibiting activity, for the treatment of e.g. endothelin dependent hypertension, cardiac and cerebral ischemia, endothelin dependent asthma and endothelin dependent renal failure.

The pharmaceutical compositions according to the invention are those suitable for enteral, such as oral or rectal, transdermal and parenteral administration to mammals, including man, for the treatment of e.g. cardiovascular disorders, such as hypertension, cardiac cerebral ischemia, comprising an effective amount of a pharmacologically active compound of the invention or a pharmaceutically acceptable salt thereof, alone or in combination with one or more pharmaceutically acceptable carriers.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g. lactose, dextrose, sucrose, mannitol, sorbitol, cellulose and/or glycine; b) lubricants, e.g. silica, talcum, stearic acid, its magnesium or calcium salts and/or polyethyleneglycol; for tablets also c) binders, e.g. magnesium aluminum silicate, starch paste, gelatin, tragacanth, methylcellulose, sodium carboxymethylcellulose and/or polyvinylpyrrolidone; if desired, d) disintegrants, e.g. starches, agar, alginic acid or its sodium salt, or effervescent mixtures; and/or e) absorbents, colorants, flavors and sweeteners. Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, the compositions may also contain other therapeutically valuable substances. Said compositions are prepared according to conventional mixing, granulating or coating methods, respectively, and contain about 0.1 to 75%, preferably about 1 to 50%, of the active ingredient.

Suitable formulations for transdermal application include an effective amount of a compound of the invention with carrier. Advantageous carriers include absorbable pharmacologically acceptable solvents to assist passage through the skin of the host. Characteristically, transdermal devices are in the form of a bandage comprising a backing member, a reservoir containing the compound, optionally with carriers, optionally a rate controlling barrier to deliver the compound to the skin of the host at a controlled and predetermined rate over a prolonged period of time, and means to secure the device to the skin.

A unit dosage for a mammal of about 50 to 70 kg may contain between about 5 and 100 mg of the active ingredient. The dosage of active compound is dependent on the species of warm-blooded animal (mammal), the body weight, age and individual condition, and on the form of administration.

The following examples are intended to illustrate the invention and are not to be construed as being limitations thereon. Temperatures are given in degrees Centigrade. If not mentioned otherwise, all evaporations are performed under reduced pressure, preferably between about 15 and 100 mm Hg. Optical rotations are measured at room temperature at 589 nm (D line of sodium) or other wavelengths as specified in the examples.

The prefixes R and S are used to indicate the absolute configuration at each asymmetric center and the corresponding enantiomers.

The tetrazole derivatives are named as 1-H or 1-substituted compounds. However, such may exist as tautomeric 2-H or 2-substituted compounds or as a mixture of said tautomeric forms.

EXAMPLE 1

To a stirred solution of (S)-[2-(biphenyl-4-yl)-1-(1H-tetrazol-5-yl)-ethylamino]-methylphosphonic acid dimethyl ester (0.41 g, 1.06 mmol) in acetic acid (3.5 mL) heated to 90° is added 9N HCl (15 mL). Heating is continued for 12.5 hours, then the reaction mixture is stirred at room temperature for 12 hours. The excess of HCl is removed under reduced pressure, then water is added. The solid is filtered off and washed with water, then ether. The solid is dried at 70° under high vacuum for 4 hours then at room temperature for 18 hours. (S)-[2-(Biphenyl-4-yl)-1-(1H-tetrazol-5-yl)-ethylamino]-methylphosphonic acid is obtained as a colorless powder, m.p.: 272° (dec), $[\alpha]_D=+58.4°$ (c 0.9, 0.1N NaOH).

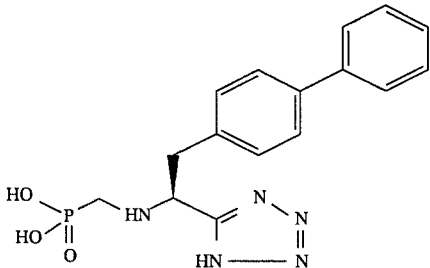

The starting material is prepared as follows:

(S)-2-t-Butoxycarbonylamino-3-biphenyl-4-yl-propionic acid (J. Org. Chem., 1992, 57, 379; 20 g, 58 mmol) in ethyl acetate (300 mL) and methylene chloride (75 mL) is cooled under nitrogen to 0° with an ice bath and treated with N-methylmorpholine (6.5 mL, 58 mmol). Isobutyl chloroformate (7.6 mL, 58 mmol) is added dropwise. After 5 minutes of stirring, 3-aminopropionitrile (4.52 g, 64 mmol) in methylene chloride (50 mL) is added over 4 minutes. Stirring is continued for 1 hour at 0° then for 4 hours at room temperature. Ethyl acetate (300 mL) is added and the solution is successively washed with cold water (100 mL), saturated sodium bicarbonate (100 mL) and water (100 mL). The organic layer is dried over anhydrous sodium sulfate, filtered and concentrated under reduced pressure. The residue is triturated with ether (150 mL). The solid is filtered off, washed with cold ether and dried under high vacuum to give (S)-2-t-butoxycarbonylamino-3-biphenyl-4-yl-N-(2-cyanoethyl)-propionamide as a colorless crystalline solid, m.p. 163°–164°; $[\alpha]_D=+3.58°$ (c 1, CHCl$_3$).

To a stirred solution of (S)-2-t-butoxycarbonylamino-3-biphenyl-4-yl-N-(2-cyanoethyl)-propionamide (18 g, 45.7 mmol) in THF (375 mL) under nitrogen is added triphenylphosphine (12 g, 45.7 mmol). The solution is cooled to 0° and treated with diethyl azodicarboxylate (DEAD, 7.2 mL, 24.3 mmol) followed by trimethylsilyl azide (3.2 mL, 24.3 mmol). The solution is warmed up to room temperature and stirred for 18 hours. One additional equivalent of triphenyl phosphine (12 g, 45.7 mmol), DEAD (7.2 mL, 24.3 mmol) and trimethylsilyl azide (3.2 mL, 24.3 mmol) are added and stirring is continued for 3 days. The solution is cooled to 0°. Ceric ammonium nitrate (2.2 L; 10% aqueous solution) is added dropwise. After 20 minutes of stirring, extraction is carried out with methylene chloride (3×200 mL). The combined organic layers are dried over anhydrous sodium sulfate, then filtered and concentrated in vacuo. The residue is taken up in ethyl acetate (500 mL) and hexane (50 mL). A small amount of (S)-3-[5-(1-t-butoxycarbonylamino-2-biphenyl-4-yl-ethyl)-tetrazol-1-yl]-propionitrile crystallizes out. The filtrate is concentrated and the residue purified by flash-chromatography eluting with a gradient of ethyl acetate in hexane (30% to 50%). The pure fractions of product (Rf=0.6 in 1/1 ethyl acetate/hexane) are combined and concentrated under reduced pressure to give (S)-3-[5-(1-t-butoxycarbonylamino-2-biphenyl-4-yl-ethyl)-tetrazol-1-yl]-propionitrile as a colorless crystalline solid, m.p. 184°–185°, $[\alpha]_D=-2.90°$ (c 0.89, CHCl$_3$).

(S)-3-[5-(1-t-butoxycarbonylamino-2-biphenyl-4-yl-ethyl)-tetrazol-1-yl]-propionitrile can also be prepared as follows:

To a stirred solution of (S)-2-t-butoxycarbonylamino-3-biphenyl-4-yl-N-(2-cyanoethyl)-propionamide (20 g, 51.2 mmol) in acetonitrile (220 mL) under nitrogen is added triphenyl phosphine (33.6 g, 128 mmol). The suspension is cooled to 0°. Diisopropyl azodicarboxylate (24.8 mL, 125.6 mmol) is placed in an addition funnel. In a separate addition funnel is placed trimethylsilyl azide (16.8 mL, 127.2 mmol). The two reagents are introduced dropwise, allowing the azoester to be added about 1 minute faster than the silyl azide and keeping the reaction temperature below 10°. The slightly yellow suspension is gradually (10°/hour) warmed up to 35°. The reaction is then monitored by TLC (ethyl acetate/hexane:3/1) until practically complete conversion is observed. A clear solution is then usually obtained. The excess of azide is destroyed by cooling the solution to 10° and adding sodium nitrite (3.2 g) in water (16 mL), followed by acetic acid (16 mL). The mixture is stirred at 20°–25° for at least 2 hours, until a nitrite-free aliquot of the acetonitrile layer shows a negative zide test (ferric chloride paper). The lower salt phase is separated and the organic layer is concentrated in vacuo at 45°. The semi-solid residue is dissolved in isopropanol at 80°. Some insoluble material is filtered from the hot solution. The title compound crystallizes at about 60° after seeding. The suspension is cooled to 25° within 2 hours then left at 0°–5° for 1 hour. The product is filtered, washed with cold ispropanol (3×20 mL) and dried under reduced pressure at 50° to constant weight to obtain (S)-3-[5-(1-t-butoxycarbonylamino-2-biphenyl-4-yl-ethyl)-tetrazol-1-yl]-propionitrile.

(S)-3-[5-(1-t-butoxycarbonylamino-2-biphenyl-4-yl-ethyl)-tetrazol-1-yl]-propionitrile (9.22 g, 22 mmol) is dissolved in methylene chloride (135 mL) under nitrogen. To the stirred solution is added trifluoroacetic acid (50 mL). After 50 minutes, the solution is concentrated under reduced pressure and the residue is treated with ether (200 mL). The amorphous solid is filtered off, washed with ether and dried under vacuum at 45° for 2 hours, then at room temperature for 18 hours to yield (S)-3-[5-(1-amino- 2-biphenyl-4-yl-ethyl)-tetrazol-1-yl]]-propionitrile trifluoroacetate salt, m.p. 211°–212°, $[\alpha]_D=+23.35°$ (c 1.05, DMSO).

(S)-3-[5-(1-amino-2-biphenyl-4-yl-ethyl)-tetrazol-1-yl]-propionitrile trifluoroacetate salt (1.0 g, 2.3 mmol) is suspended in saturated sodium bicarbonate (10 mL) and extracted in methylene chloride (2×25 mL). The organic layer is dried over anhydrous sodium sulfate, filtered and concentrated in vacuo to give the corresponding free base as an amorphous solid (0.73 g, 100%). The latter is dissolved in methylene chloride (8 mL) and treated with diisopropylethyl-amine (0.57 mL, 3.29 mmol). To the solution at 0° is added dimethylphosphonomethyl trifluoromethylsulfonate (Tetrahedron Lett., 1986, 1477) (0.81 g, 2.99 mmol) and the reaction mixture is stirred for 75 minutes. After warming to room temperature, stirring is continued for 24 hours. Ethyl acetate (60 mL) is added and the solution is washed successively with cold 1N HCl (20 ml), water, cold sodium bicarbonate solution and water. The organic layer is dried over anhydrous sodium sulfate, filtered and concentrated in vacuo. The residue is purified by flash-chromatography using a gradient of methanol (0 to 1%) in ethyl acetate as eluent. (S)-[1-[1-(2-Cyanoethyl)-1H-tetrazol-5-yl]-2-(biphenyl-4-yl)-ethylamino]-methylphosphic acid dimethyl ester is obtained as a colorless oil, $[\alpha]_D=+3.76°$ (c 0.77, $CHCl_3$).

To a solution of (S)-[1-[1-(2-cyanoethyl)-1H-tetrazol-5-yl]-2-(biphenyl-4-yl)-ethylamino]-methylphosphonic acid dimethyl ester (580 mg, 1.32 mmol) in THF (6 mL) and methanol (6 mL) is added dropwise 1N sodium hydroxide (1.52 mL, 1.52 mmol). After 2 hours, the reaction mixture is treated with 1N hydrochloric acid (1.8 mL, 1.8 mmol). The organic solvents are removed by concentration under reduced pressure and the residue is treated with water (5 mL) and extracted with methylene chloride (3×15 mL). The combined organic layers are dried over anhydrous sodium sulfate, filtered and concentrated in vacuo. (S)-[2-Biphenyl-4-yl-1-(1H-tetrazol-5-yl)-ethylamino]-methylphosphonic acid dimethyl ester is crystallized from ether, m.p.: 117°–118°, $[\alpha]_D=-34.67°$ (c 0.8, $CHCl_3$).

EXAMPLE 2

Similarly to the procedures in example 1, the following are prepared:
1) (S)-[2-(2-methoxy-biphenyl-4-yl)-1-(1H-tetrazol-5-yl)-ethylamino]-methylphosphonic acid; m.p.: 239°–241° (dec.), $[\alpha]_D=25.81°$ (c 0.61, NaOH 1N), being the compound of formula III wherein $R_4$ is 2-methoxy.
2) (S)-[2-(2'-methoxy-biphenyl-4-yl)-1-(1H-tetrazol-5-yl)-ethylamino]-methylphosphonic acid; m.p.: 250° (dec.), being the compound of formula III wherein $R_4'$ is 2'-methoxy.

The starting protected amino acid, (S)-2-t-butoxycarbonylamino-3-(2'-methoxy-biphenyl-4-yl)-propionic acid, is prepared as follows:

To a cold (−78°) solution of n-butyllithium (2.5M in hexane, 5.1 mL, 12.8 mmol) in dry THF (20 mL) under nitrogen is added dropwise 2-bromoanisole (1.3 mL, 10.7 mmol). The mixture is stirred for 45 minutes, then treated with trimethylborate (3.64 mL, 32 mmol). The solution is allowed to warm up to room temperature and stirring is continued for 18 hours. A 0.5% HCl solution is added to reach pH 6.5. The product is extracted in methylene chloride (2×40 mL). The organic layer is dried over anhydrous sodium sulfate, filtered and concentrated in vacuo. The residue is triturated with hexane to give the boronic acid as a white solid (m.p. 102°). Palladium-catalyzed coupling to (S)-N-tBOC tyrosine O-trifluoromethanesulfonate methyl ester is carried out according to J. Org. Chem., 1992, 57, 379 to give (S)-2-t-butoxycarbonylamino-3-(2'-methoxy-biphenyl-4-yl)-propionic acid methyl ester.

A solution of (S)-N-t-butoxycarbonylamino-3-(2'-methoxybiphenyl-4-yl)-propionic acid methyl ester (4.1 g in methanolic 1N sodium hydroxide (60 mL) is stirred at room temperature for 3 hours. Ether (30 mL) and water (30 mL) are added. The aqueous layer is separated and acidified with concentrated HCl, then extracted with ether (2×20 mL) and dried over anhydrous sodium sulfate. Evaporation of the solvent under reduced pressure gives (S)-N-t-butoxycarbonylamino-3-(2'-methoxybiphenyl-4-yl)-propionic acid.
3) (S)-[2-(3-methoxy-biphenyl-4-yl)-1-(1H-tetrazol-5-yl)-ethylamino]-methylphosphonic acid;
4) (S)-[2-(3'-methoxy-biphenyl-4-yl)-1-(1H-tetrazol-5-yl)-ethylamino]-methylphosphonic acid.

EXAMPLE 3

To a solution of (S)-[1-[1-(2-cyanoethyl)-1H-tetrazol-5-yl]-2-(biphenyl- 4-yl)-ethylamino-methylphosphonic acid diphenyl ester (0.5 g; 0.89 mmol) in methylene chloride (10 mL) under nitrogen is added 1,8-diazabicyclo[5.4.0]undec-7-ene (DBU, 0.66 mL; 4.4 mmol). After 3 hours, the solution is diluted with ethyl acetate (60 mL), washed with ice cold HCl 1N (15 mL) and water (2×15 mL). The organic phase is dried over magnesium sulfate and filtered through a plug of silica gel to remove traces of polar impurities. The silica gel is washed with ethyl acetate (125 mL), then with methylene chloride/methanol (95/5) (20 mL). The solvents are removed under reduced pressure to give a glassy residue which is redissolved in warm ethyl acetate (5 mL) and treated with hexane (5 mL). Crystallization occurs upon cooling to 0° for 45 minutes. The solid is filtered off, washed with ethyl acetate/hexane (1/1) and dried under high vacuum for 1 hour at 45° and 20 hours at room temperature. (S)-[2-Biphenyl-4-yl-1-(1H-tetrazol- 5-yl)-ethylamino]-methylphosphonic acid diphenyl ester is obtained as a colorless crystalline solid, m.p.: 128°–129°, $[\alpha]_D=-39.5°$ (c 0.86, $CHCl_3$).

The starting material is prepared as follows:

(S)-3-[5-(1-amino -2-biphenyl-4-yl-ethyl)-tetrazol-1-yl]-propionitrile trifluoroacetate salt (2.5 g, 5.7 mmol) is suspended in ice cold saturated sodium bicarbonate (50 mL) and the free base is extracted with methylene chloride (3×25 mL). The organic layer is dried over magnesium sulfate, filtered and concentrated in vacuo. To the residue (free base) dissolved in ethyl acetate (25 mL) at 0° is added an aqueous solution of formaldehyde (0.6 mL; 37% in water, 8 mmol). The reaction mixture is warmed up to room temperature over 2 hours and stirred for 14 hours. Cold water is added (40 mL) and the organic layer is dried over anhydrous sodium sulfate, filtered and concentrated under reduced pressure to give the hexahydrotriazine as a colorless amorphous solid which is dried under high vacuum. To the crude hexahydrotriazine (1.7 g; 5.13 mmol) in toluene (25 mL) and THF (10 mL) under nitrogen is added diphenyl phosphite (1.5 mL; 6.15 mmol). The mixture is heated to 70° for 90 minutes then at room temperature for 18 hours. THF is evaporated in vacuo and the residue taken up in ethyl acetate (30 mL), washed with cold 0.5N HCl (15 mL), water (15 mL) and brine (15 mL). The organic layer is dried over sodium sulfate, filtered and concentrated under reduced pressure. The oily residue is dissolved in warm (40°–45°) ethyl acetate. Hexane (30 mL) is added. The product crystallizes slowly, and the mixture is cooled to 0° for 18 hours. The solid is filtered off and washed with ethyl acetate/hexane (1/1) before being dried under high vacuum at 45°. (S)-[1-[1-(2-Cyanoethyl)-1H-tetrazol-5-yl]-2-(biphenyl-4-yl)-ethylamino]-methylphosphonic acid diphenyl ester is obtained as a colorless crystalline solid, m.p.: 133°–134°, $[\alpha]_D=-12.59°$ (c 0.94, CHCl$_3$).

EXAMPLE 4

Similarly prepared according to the procedures described in example 3 are:
1) (S)-[2-Biphenyl-4-yl-1-(1H-tetrazol-5-yl)-ethylamino]-methylphosphonic acid di-3-methylphenyl ester, The starting di-(3-methylphenyl)phosphite is prepared as follows:

To a stirred solution of m-cresol (5.1 g, 47 mmol) in methylene chloride (5 mL) cooled to 0° under nitrogen is added methanol (0.97 mL, 24 mmol). Phosphorus trichloride (2 mL, 23 mmol) is then added dropwise over 20 minutes. The flask is vented to allow the hydrochloric acid formed to excape, then the mixture is allowed to warm up slowly to room temperature and stirred to 10 hours. The solvent is removed under reduced pressure and the residue is dried under high vacuum to yield di-(3-methylphenyl)phosphite.

Other diaryl phosphites used as starting materials for compounds listed below are similarly prepared from the corresponding substituted phenol.
2) (S)-[2-Biphenyl-4-yl-1-(1H-tetrazol-5-yl)-ethylamino]-methylphosphonic acid di-3,5-dimethylphenyl ester, m.p.: 64°–67°, $[\alpha]_D=-32.71°$ (c 0.75, CHCl$_3$);
3) (S)-[2-Biphenyl-4-yl-1-(1H-tetrazol-5-yl)-ethylamino]-methylphosphonic acid di-3-methoxyphenyl ester;
4) (S)-[2-Biphenyl-4-yl-1-(1H-tetrazol-5-yl)-ethylamino]-methylphosphonic acid di-4-acetamidophenyl ester;
5) (S)-[2-(2-methoxybiphenyl-4-yl)-1-(1H-tetrazol-5-yl)-ethylamino]-methylphosphonic acid diphenyl ester,
6) (S)-[2-(2'-methoxy-biphenyl-4-yl)-1-(1H-tetrazol- 5-yl)-ethylamino]-methylphosphonic acid diphenyl ester;
7) (S)-[2-(3-methoxy-biphenyl-4-yl)-1-(1H-tetrazol-5-yl)-ethylamino]-methylphosphonic acid diphenyl ester;
8) (S)-[2-(3'-methoxy-biphenyl-4-yl)-1-(1H-tetrazol-5-yl)-ethylamino]-methylphosphonic acid diphenyl ester.

EXAMPLE 5

To a stirred solution of (S)-[2-biphenyl-4-yl-1-(1H-tetrazol-5-yl)-ethylamino]-methylphosphonic acid diphenyl ester (0.36 g, 0.7 mmol) in THF (7 mL) is added 2N HCl (3.5 mL). After stirring at room temperature for 18 hours, the precipitate is filtered off, washed with THF/water (1/1) (5 mL) then water (10 mL). The solid is stirred in ethyl acetate (3 mL) for 1.5 hours, filtered and dried under vacuum. (S)-[2-Biphenyl-4-yl-1-(1H-tetrazol-5-yl)-ethylamino]-methylphosphonic acid monophenyl ester is obtained as a colorless solid, m.p.: 262° (dec), $[\alpha]_D=+9.76°$ (c 0.76, TFA).

EXAMPLE 6

Similarly prepared according to the procedure described in example 5 are:
1) (S)-[2-Biphenyl-4-yl-1-(1H-tetrazol-5-yl)-ethylamino]-methylphosphonic acid mono-3,5-dimethylphenyl ester,
2) (S)-[2-Biphenyl-4-yl-1-(1H-tetrazol-5-yl)-ethylamino]-methylphosphonic acid mono-3-methylphenyl ester,
3) (S)-[2-Biphenyl-4-yl-1-(1H-tetrazol-5-yl)-ethylamino]-methylphosphonic acid mono-3-methoxyphenyl ester,
4) (S)-[2-Biphenyl-4-yl-1-(1H-tetrazol-5-yl)-ethylamino]-methylphosphonic acid mono-4-acetamidophenyl ester,
5) (S)-[2-(2-methoxy-biphenyl-4-yl)-1-(1H-tetrazol-5-yl)-ethylamino]-methylphosphonic acid monophenyl ester,
6) (S)-[2-(2'-methoxy-biphenyl-4-yl)-1-(1H-tetrazol-5-yl)-ethylamino]-methylphosphonic acid monophenyl ester,
7) (S)-[2-(3-methoxy-biphenyl-4-yl)-1-(1H-tetrazol-5-yl)-ethylamino]-methylphosphonic acid monophenyl ester,
8) (S)-[2-(3'-methoxy-biphenyl-4-yl)-1-(1H-tetrazol-5-yl)-ethylamino]-methylphosphonic acid monophenyl ester.

EXAMPLE 7

(S)-[2-Biphenyl-4-yl-1-[1-(2-cyanoethyl)-1H-tetrazol-5-yl]-ethylamino]-methylphosponic acid di-(ethoxycarbonylmethyl) ester (2.96 g, 5.06 mmol) is dissolved in methylene chloride (35 mL) under nitrogen and treated with DBU (3.8 mL, 25.3 mmol). The resulting pale yellow solution is stirred at room temperature for 3.5 hours. The reaction mixture is added to a well stirred mixture of ice and 0.5M sodium dihydrogenophosphate (75 mL). The organic phase is separated. The aqueous layer is extracted with methylene chloride (2×25 mL). The combined organic layers are dried over magnesium sulfate and filtered through a plug of silica gel. After washing the silica gel with 3% of methanol in methylene chloride, the filtrate is concentrated in vacuo and the residue purified by flash-chromatography, eluting with 4% of methanol in methylene chloride. (S)-[2-Biphenyl-4-yl-1-[1H-tetrazol-5-yl]-ethylamino]-methylphosphonic acid di-(ethoxycarbonylmethyl) ester is recrystallized from ethyl acetate-hexane to give a colorless crystalline solid; m.p.: 123°–124°, $[\alpha]_D=-43.68°$ (c 0.76, CHCl$_3$).

The starting material is prepared as follows:

To a stirred solution of ethyl glycolate (7.2 g, 69 mmol) in cold (ice bath) methylene chloride (8 mL) is added dropwise phosphorus trichloride (2 mL, 23 mmol). The solution is stirred at room temperature for 16 hours. The solution is concentrated under high vacuum and the obtained crude di-(ethoxycarbonylmethyl)phosphite is used directly.

Alternately, di-(ethoxycarbonylmethyl)phosphite can be prepared as follows:

To a stirred solution of dry phosphorous acid (1 g, 12.2 mmol) in anhydrous acetonitrile (10 mL) under nitrogen, is added at 0° diisopropyl ethylamine (4.25 mL) followed by ethyl bromoacetate (2.72 mL, 24.4 mmol). The mixture is allowed to warm slowly to room temperature and stirred for 18 hours. The solvent is removed under reduced pressure and the residue taken in ethyl acetate. The solid material is filtered off and the filtrate is washed successively with cold 1N hydrochloric acid and water. The organic layer is dried over anhydrous magnesium sulfate, filtered and concentrated in vacuo. The residue is dried under high vacuum, yielding the title product as an amber oil characterized by H$^1$-NMR in CDCl$_3$ (P—H: 7.23 ppm, J=625 Hz).

A solution of the hexahydro-triazine obtained in example 3 (3.2 g, 9.66 mmol) in toluene (30 mL) is treated with di-(ethoxycarbonylmethyl)phosphite (3.2 g, 12.6 mmol) and the solution is heated under nitrogen to 70° for 1.5 hours, then stirred at room temperature for 20 hours. The solution is diluted with ethyl acetate (30 mL), washed successively with cold water, cold HCl 0.5N (30 mL), cold water (2×25 mL) and dried over anhydrous sodium sulfate. The filtrate is concentrated and the residue purified by flash-chromatography, eluting with a gradient of ethyl acetate in hexane (70% to 75%). (S)-[2-Biphenyl-4-yl-1-[1-(2-cyanoethyl)-1H-tetrazol-5-yl]-ethylamino]-methylphosphonic acid di-(ethoxycarbonylmethyl) ester is obtained as a colorless oil.

EXAMPLE 8

Similarly prepared according to the procedures described in example 7 are:
1) (S)-[2-biphenyl-4-yl-1-[1H-tetrazol-5-yl]-ethylamino]-methylphosphonic acid di-(isopropyloxycarbonylmethyl) ester, oil;
2) (S)-[2-biphenyl-4-yl-1-[1H-tetrazol-5-yl]-ethylamino]-methylphosphonic acid di-(N,N-dimethyl-carbamoylmethyl) ester, m.p. 115°–119°;
3) (S)-[2-biphenyl-4-yl-1-[1H-tetrazol-5-yl]-ethylamino]-methylphosphonic acid di-(2-trichloroethyl) ester;
4) (S)-[2-(2-methoxy-biphenyl-4-yl)-1-(1H-tetrazol-5-yl)-ethylamino]-methylphosphonic acid di-(ethoxycarbonylmethyl) ester;
5) (S)-[2-(2'-methoxy-biphenyl-4-yl)-1-(1H-tetrazol-5-yl)-ethylamino]-methylphosphonic acid di-(ethoxycarbonylmethyl) ester;
6) (S)-[2-(3-methoxy-biphenyl-4-yl)-1-(1H-tetrazol-5-yl)-ethylamino]-methylphosphonic acid di-(ethoxycarbonylmethyl) ester;
7) (S)-[2-(3'-methoxy-biphenyl-4-yl)-1-(1H-tetrazol-5-yl)-ethylamino]-methylphosphonic acid di-(ethoxycarbonylmethyl) ester.

EXAMPLE 9

(a) To a stirred solution of (R)-[1-[1-(2-cyanoethyl)-1H-tetrazol-5-yl]-2-(biphenyl-4-yl)-ethylamino]-methylphosphoic acid diphenyl ester (0.35 g, 0.62 mmol) in methanol (6 mL) under nitrogen, is added potassium fluoride (0.36 g, 6.2 mmol) and 18-crown-6 (25 mg, 0.09 mmol). The solution is warmed in a pre-heated oil bath at 80° and refluxed gently for 10 minutes and then cooled to room temperature. 1N Hydrochloric acid (5 mL) is added and the methanol is removed under reduced pressure. The residue is treated with water (10 mL) and extracted with methylene chloride (3×10 mL). The combined organic layers are dried over anhydrous magnesium sulfate, filtered and concentrated in vacuo. The residue is dissolved in a 1/1 mixture of methanol and THF (6 mL) and treated with 1N sodium hydroxide (1.06 mL, 1.06 mmol). After 100 minutes of stirring, the solution is treated with 1N hydrochloric acid (1.2 mL, 1.2 mmol) and the organic solvents are evaporated in vacuo. Water (5 mL) is added and the aqueous layer is extracted with methylene chloride (3×10 mL). The combined organic phases are dried over anhydrous magnesium sulfate, filtered and concentrated under reduced pressure. The solid residue is triturated with ether to afford (R)-[2-biphenyl-4-yl)-1-(1H-tetrazol-5-yl)-ethylamino]-methylphosphonic acid dimethyl ester, $[\alpha]_D$=+34.36 (c 0.84, CHCl$_3$).

Hydrolysis according to example 1 yields (R)-[2-biphenyl-4-yl)-1-(1H-tetrazol-5-yl)-ethylamino]-methylphosphonic acid.

(b) Similarly prepared is the corresponding (S)-enantiomer of example 1.

EXAMPLE 10

Similarly prepared according to procedures in the previous examples are:

(1) (S)-[3-(biphenyl-4-yl)-1-(1H-tetrazol-5-yl)-prop-2-ylamino]methylphosphonic acid.

The starting material is prepared as follows:

Similarly to a method reported in *J. Med. Chem.*, 1988, 31, 2199, to a stirred solution of (S)-2-t-butoxycarbonylamino-3-(biphenyl-4-yl)-propionic acid (*J. Org. Chem.*, 1992, 57, 379; 1 g, 2.93 mmol) in THF (10 mL) at 0° is added N-methylmorpholine (0.35 mL, 3.18 mmol), followed by isobutyl chloroformate (0.39 mL, 3.0 mmol). The suspension is stirred for 1 hour, then filtered. The precipitate is washed with dry ether (5 mL). A saturated solution of diazomethane in ether is added at 0° until persistence of a yellow color. After stirring for 1 hour at 0° and 1 hour at room temperature, the solution is concentrated in vacuo to yield the intermediate diazoketone as a beige solid (m.p. 128°–129°). The solid is suspended in methanol (10 mL). A solution of silver benzoate (150 mg, 0.65 mmol) in triethylamine (3 mL) is added dropwise. The dark solution is stirred at room temperature for 30 minutes, then filtered through Celite. The filtrate is concentrated under reduced pressure and the residue is redissolved in ethyl acetate (20 mL). The organic layer is washed successively with water (10 mL), saturated sodium bicarbonate (10 mL) and 1N hydrochloric acid (10 mL) before being dried over anhydrous sodium sulfate and filtered. After evaporation of the solvent in vacuo, the residue is purified by flash-chromatography on silica gel, eluting with 25% ethyl acetate in hexane. (S)-3-t-Butoxycarbonylamino-4-(biphenyl-4-yl)-butyric acid methyl ester is obtained as a solid, m.p. 86°–87°.

Hydrolysis with methanolic 1N sodium hydroxide yields the carboxyclic acid which is then converted to the product using methodology similar to that described in example 1.
(2) (S)-[4-(biphenyl-4-yl)-1-(1H-tetrazol-5-yl)-butyl-3-amino]-methylphosphonic acid The starting material is prepared as follows:

Similarly to a method reported in *Tetrahedron Lett.*, 1991, 923, to a stirred solution of (S)-2-t-butoxycarbonylamino-3-(biphenyl-4-yl)-propionic acid (3 g, 8.8 mmol) in dimethoxyethane (DME; 8 mL) at −15° is added N-methylmorpholine (0.975 mL, 8.8 mmol), followed by isobutyl chloroformate (1.2 mL, 9.25 mmol). After 5 minutes, the precipitate is removed by filtration and washed with DME (5 mL). The filtrate is cooled to 0° and treated at once with a freshly prepared clear solution of sodium borohydride (500 mg) in water (5 mL). After the strong evolution of gas has ceased, water (100 mL) is added and the product is extracted in ethyl acetate. The organic layer is separated, dried over magnesium sulfate, decolorized with activated charcoal, filtered and concentrated in vacuo to yield (S)-2-(t-butoxycarbonylamino)-3-(biphenyl-4-yl)-propan-1-ol as a white solid, m.p.: 116°, $[\alpha]_D$=−22.90 (c 0.74, MeOH).

To a solution of oxalyl chloride (0.535 mL, 6.14 mmol) in methylene chloride (3 mL) cooled to −70° under nitrogen is added dropwise dimethylsulfoxide (0.830 mL, 10.7 mmol) im methylene chloride (3 mL). After 20 minutes of stirring at −70°, a solution of (S)-2-t-butoxycarbonylamino-3-(biphenyl-4-yl)-propan-1-ol (1 g, 3.05 mmol) in methylene chloride (3 mL) is added, followed by triethylamine (2 mL, 14.3 mmol). The solution is allowed to warm up to room temperature over a 1 hour period then poured into brine. Methylene chloride (50 mL) and water (80 mL) are added. The organic layer is separated, dried over anhydrous magnesium sulfate, filtered and concentrated in vacuo. The crude aldehyde is dissolved in methylene chloride (15 mL) and treated with (carboethoxymethylene)-triphenylphosphorane (2.1 g, 6.1 mmol). After stirring at room temperature for 18 hours, silica gel (2 g) is added and the solvent is evaporated under vacuum. The product is purified by flash-chromatography on silica gel, eluting with 25% ethyl acetate in hexane. (S)-4-(t-Butoxycarbonylamino)-5-(biphenyl-4-yl)-pentenoic acid ethyl ester is obtained a white solid, m.p. 91°–94°.

Catalytic hydrogenation, e.g. with palladium on charcoal, and hydrolysis with methanolic 1N sodium hydroxide yields (S)-4-(t-butoxycarbonylamino)-5-(biphenyl-4-yl)-pentanoic acid, and such is then converted to the product using methodology similar to that described in example 1.

EXAMPLE 11

(S)-3-(Biphenyl-4-yl)-2-(dimethylphosphonomethylamino)-propionic acid (278 mg, 0.76 mmol) is dissolved in a 30% solution of hydrobromic acid in acetic acid (10 mL) under nitrogen. After 2 hours, ether (50 mL) is added and the product precipitates. The mixture is kept at 0° for 18 hours and then filtered. The solid is dissolved in 0.1N sodium hydroxide (25 mL) and the insoluble material is filtered. The filtrate is acidified with 2N hydrochloric acid (5 mL). The gelatinous solid is filtered, washed with water and dried under high vacuum at 75° to give the (S)-3-(biphenyl-4-yl)-2-(phosphonomethylamino)-propionic acid as a white powder; m.p.: 241° (dec.); $[\alpha]_D=+33.16$ (c 0.95, 0.1N NaOH).

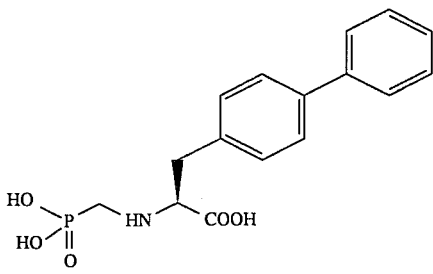

The starting material is prepared as follows:

To a suspension of (S)-2-amino-3-(biphenyl-4-yl)-propionic acid methyl ester hydrochloride (J. Org. Chem., 1992, 57, 379; 10 g, 34.3 mmol) in water (200 mL) is added solid sodium bicarbonate (3.17 g, 37.7 mmol). The mixture is stirred for 30 minutes and then extracted with ether (3×80 mL). The combined organic phases are washed with brine (50 mL) and then dried over anhydrous magnesium sulfate. Evaporation of the solvent in vacuo affords (S)-2-amino-3-(biphenyl-4-yl)-propionic acid methyl ester as a white solid.

(S)-2-Amino-3-(biphenyl-4-yl)-propionic acid methyl ester (5 g, 19.6 mmol) is dissolved in methylene chloride (100 mL) at 0°. Diisopropyl ethylamine (3.74 mL, 21.5 mmol) is added, followed by a solution of dimethylphosphonomethyl trifluoromethylsulfonate (Tetrahedron Lett., 1986, 1477; 5.86 g, 21.5 mmol). The mixture is stirred for 2 hours, warmed to room temperature and stirred for 16 hours. The solution is washed with saturated sodium bicarbonate, water and brine. The organic layer is dried over anhydrous sodium sulfate, filtered and concentrated in vacuo. The residue is purified by flash-chromatography to afford an amber oil which solidifies upon standing, such being (S)-3-(biphenyl-4-yl)-2-[(dimethylphosphonomethyl)-amino]-propionic acid methyl ester, $[\alpha]_D=+1.16$ (c 0.77, MeOH).

(S)-3-(Biphenyl-4-yl)-2-[(dimethylphosphonomethyl)-amino]-propionic acid methyl ester (5 g, 13.2 mmol) is dissolved in methanol (60 mL) and cooled to 0°. 1N Sodium hydroxide (19.8 mL, 19.8 mmol) is added dropwise. The solution is stirred at room temperature for 4 hours, then neutralized with 1N hydrochloric acid (20.2 mL, 20.2 mmol). The solvent is removed in vacuo at 10° from the gelatinous solution. The residue is extracted with methylene chloride (3×20 mL). The combined organic layers are washed with brine, dried over anhydrous magnesium sulfate, filtered and concentrated in vacuo. The crude solid is triturated with acetonitrile, filtered and washed with ether. (S)-3-(Biphenyl-4-yl)-2-[(dimethylphosphonomethyl)-amino]-propionic acid is obtained as a white solid that is dried under vacuum at 60° for 16 hours, $[\alpha]_D=+77.34$ (c 0.83, MeOH).

EXAMPLE 12

According to the procedures in example 11, the following aminophosphonic acids can be prepared:

(1) (S)-3-(2-Methoxy-biphenyl-4-yl)-2-(phosphonomethylamino)-propionic acid, m.p.: 205°–208°, $[\alpha]_D=+5.99$ (c 0.61, 1N NaOH).

(2) (S)-3-(2'-Methoxy-biphenyl-4-yl)-2-(phosphonomethylamino)-propionic acid.

The starting material is prepared as follows:

To a cold (−78°) solution of n-butyllithium (2.5M in hexane, 5.1 mL, 12.8 mmol) in dry THF (20 mL) under nitrogen is added dropwise 2-bromoanisole (1.3 mL, 10.7 mmol). The mixture is stirred for 45 minutes, then treated with trimethylborate (3.64 mL, 32 mmol). The solution is allowed to warm up to room temperature and stirring is continued for 18 hours. A 0.5% HCl solution is added to reach pH 6.5. The product is extracted in methylene chloride (2×40 mL). The organic layer is dried over anhydrous sodium sulfate, filtered and concentrated in vacuo. The residue is triturated with hexane to give the boronic acid as a white solid (m.p. 102°). Palladium-catalyzed coupling to (S)-N-tBOC tyrosine O-trifluoromethanesulfonate methyl ester is carried out according to J. Org. Chem., 1992, 57, 379 to give (S)-2-t-butoxycarboxylamino-3-(2'-methoxy-biphenyl-4-yl)-propionic acid methyl ester.

Treatment with a 1:1 mixture of trifluoroacetic acid and methylene chloride for 1 hour at room temperature yields (S)-2-amino-3-(2'-methoxybiphenyl-4-yl)propionic acid methyl ester.

(3) (S)-3-(3-Methoxy-biphenyl-4-yl)-2-(phosphonomethylamino)-propionic acid.

(4) (S)-3-(3'-Methoxy-biphenyl-4-yl)-2-(phosphonomethylamino)-propionic acid.

EXAMPLE 13

(S)-4-(Biphenyl-4-yl)-3-[(dimethylphosphonomethyl)-amino]-butyric acid (321 mg, 0.85 mmol) is dissolved in a 30% solution of hydrobromic acid in acetic acid (5 mL) and stirred at room temperature for 18 hours. The reaction mixture is poured into cold water (20 mL) and the white precipitate is filtered off, then redissolved in 1N sodium hydroxide (20 mL). The resulting cloudy yellow solution is filtered, then acidified with 1N hydrochloric acid (25 mL). The white precipitate is washed with water (3×20 mL), filtered and dried under high vacuum. (S)-4-(Biphenyl-4-yl)-3-(phosphonomethylamino)butyric acid hydrochloride is obtained as a white solid, m.p. 242°–244°, $[\alpha]_D=-8.79$ (c 0.72, 0.1N NaOH).

The starting material is prepared as follows:

Similarly to a method reported in J. Med. Chem., 1988, 31, 2199, to a stirred solution of (S)-2-t-butoxycarbonylamino-3-(biphenyl-4-yl)-propionic acid (J. Org. Chem., 1992, 57,379; 1 g, 2.93 mmol) in THF (10 mL) at 0° is added N-methylmorpholine (0.35 mL, 3.18 mmol), followed by isobutyl chloroformate (0.39 mL, 3.0 mmol). The suspension is stirred for 1 hour, then filtered. The precipitate is washed with dry ether (5 mL). A saturated solution of diazomethane in ether is added at 0° until persistence of a yellow color. After stirring for 1 hour at 0° and 1 hour at room temperature, the solution is concentrated in vacuo to yield the intermediate diazoketone as a beige solid (m.p. 128°–129°). The solid is suspended in methanol (10 mL). A solution of silver benzoate (150 mg, 0.65 mmol) in triethylamine (3 mL) is added dropwise. The dark solution is stirred at room temperature for 30 minutes, then filtered through Celite. The filtrate is concentrated under reduced pressure and the residue is redissolved in ethyl acetate (20 mL). The organic layer is washed successively with water (10 mL), saturated sodium bicarbonate (10 mL) and 1N hydrochloric acid (10 mL) before being dried over anhydrous sodium sulfate and filtered. After evaporation of the solvent in vacuo, the residue is purified by flash-chromatography on silica gel, eluting with 25% ethyl acetate in hexane. (S)-3-t-Butoxycarbonylamino-4-(biphenyl-4-yl)-butyric acid methyl ester is obtained as a solid, m.p. 86°–87°.

(S)-3-t-Butoxycarbonyl-amino-4-(biphenyl-4-yl)-butyric acid methyl ester (716 mg, 2 mmol) is stirred for 1 hour in a 1/1 mixture of trifluoroacetic acid and methylene chloride (5 mL). Ethyl acetate (20 mL) is added and the solution is washed with saturated sodium bicarbonate (20 mL). The organic layer is separated, dried over anhydrous sodium sulfate, filtered and concentrated in vacuo. The residue is dissolved in methylene chloride (10 mL) and cooled to 0° under nitrogen. Diisopropyl ethylamine (0.42 mL, 2.4 mmol) is added, followed by a solution of dimethylphosphonomethyl trifluoromethylsulfonate (Tetrahedron Lett., 1986, 1477; 545 mg, 2.2 mmol). The mixture is stirred for 18 hours at room temperature. The solution is washed with saturated sodium bicarbonate, water and brine. The organic layer is dried over anhydrous sodium sulfate, filtered and concentrated in vacuo. The residue is purified by flash-chromatography to afford (S)-4-(biphenyl-4-yl)- 3-[(dimethylphosphonomethyl)-amino]-butyric acid methyl ester as a white solid, m.p. 67°.

To a solution of (S)-4-(biphenyl-4-yl)-3-[(dimethylphosphonomethyl)-amino]-butyric acid methyl ester (851 mg, 2.26 mmol) in methanol (2 mL) is added 2N sodium hydroxide (1.5 mL, 3 mmol). After 1 hour of stirring, methanol is removed under vacuum and water (5 mL) is added to the residue. The aqueous layer is washed with ethyl acetate (10 mL), then acidified with 1N hydrochloric acid (4 mL). The residue is extracted with ethyl acetate (2×10 mL) and methylene chloride (10 mL). The combined organic layers are dried over anhydrous sodium sulfate, filtered and concentrated in vacuo to yield (S)-4-(biphenyl-4-yl)-3-[(dimethylphosphonomethyl)-amino]-butyric acid as a gummy solid.

EXAMPLE 14

(1) (S)-5-(Biphenyl-4-yl)-4-[(dimethylphosphonomethyl)-amino]-2-pentenoic acid ethyl ester (536 mg, 1.28 mmol) is dissolved in methanol (1 mL) and treated with 1N sodium hydroxide (2 mL, 2 mmol). The reaction mixture is stirred for 3 hours at room temperature, then 1N hydrochloric acid (5 mL) is added. The carboxylic acid is extracted in methylene chloride (20 mL). The organic layer is separated, dried over anhydrous sodium sulfate, filtered and concentrated in vacuo. The residue is suspended in methylene chloride (2 mL) under nitrogen and treated with trimethylsilyl bromide (0.424 mL, 3.21 mmol). The clear solution is stirred at room temperature for 18 hours, then concentrated in vacuo. The residue is triturated with water (5 mL) and the precipitate is filtered off and then dissolved in 1N sodium hydroxide (5 mL). 1N Hydrochloric acid (8 mL) is added to precipitate the product which is filtered and washed with water (10 mL). The solid is suspended in ethanol (5 mL) and stirred for 20 minutes with propylene oxide (2 mL). Concentration in vacuo yields (S)-5-(biphenyl-4-yl)-4-(phosphonomethylamino)-2-pentenoic acid as a white solid; m.p.: 231°–233°.

The starting material is prepared as follows:

Similarly to a method reported in Tetrahedron Lett., 1991, 923, to a stirred solution of (S)-2-t-butoxycarbonylamino-3-(biphenyl-4-yl)-propionic acid (3 g, 8.8 mmol) in dimethoxyethane (DME; 8 mL) at –15° is added N-methyl morpholine (0.975 mL, 8.8 mmol), followed by isobutyl chloroformate (1.2 mL, 9.25 mmol). After 5 minutes, the precipitate is removed by filtration and washed with DME (5 mL). The filtrate is cooled to 0° and treated at once with a freshly prepared clear solution of sodium borohydride (500 mg) in water (5 mL). After the strong evolution of gas has ceased, water (100 mL) is added and the product is extracted in ethyl acetate. The organic layer is separated, dried over magnesium sulfate, decolorized with activated charcoal, filtered and concentrated in vacuo to yield (S)-2-t-butoxycarbonylamino-3-(biphenyl-4-yl)-propan-1-ol as a white solid, m.p.: 116°, $[\alpha]_D = -22.90$ (c 0.74, MeOH).

To a solution of oxalyl chloride (0.535 mL, 6.14 mmol) in methylene chloride (3 mL) cooled to –70° under nitrogen is added dropwise dimethylsulfoxide (0.830 mL, 10.7 mmol) in methylene chloride (3 mL). After 20 minutes of stirring at –70°, a solution of (S)-2-t-butoxycarbonylamino-3-(biphenyl-4-yl)-propan-1-ol (1 g, 3.05 mmol) in methylene chloride (3 mL) is added, followed by triethylamine (2 mL, 14.3 mmol). The solution is allowed to warm up to room temperature over a 1 hour period, then poured into brine. Methylene chloride (50 mL) and water (80 mL) are added. The organic layer is separated, dried over anhydrous magnesium sulfate, filtered and concentrated in vacuo. The crude aldehyde is dissolved in methylene chloride (15 mL) and treated with (carboethoxymethylene)-triphenylphosphorane (2.1 g, 6.1 mmol). After stirring at room temperature for 18 hours, silica gel (2 g) is added and the solvent is evaporated under vacuum. The product is purified by flash-chromatography on silica gel, eluting with 25% ethyl acetate in hexane. (S)-4-(t-Butoxycarbonylamino)-5-(biphenyl-4-yl)-2-pentenoic acid ethyl ester is obtained as a white solid, m.p. 91°–94°.

(S)-4-t-Butoxycarbonylamino-5-(biphenyl-4-yl)-pentenoic acid ethyl ester (1.2 g, 3.03 mmol) is stirred for 1 hour in a 1/1 mixture of trifluoroacetic acid and methylene chloride (10 mL). A saturated aqueous solution of sodium bicarbonate (10 mL) is added and the product is extracted in methylene chloride (20 mL). The organic layer is dried over anhydrous sodium sulfate, filtered and cooled to 0° under nitrogen. To that solution is added N,N-diisopropylethylamine (0.633 mL, 3.63 mmol) in methylene chloride (2 mL), followed by a solution of dimethylphosphonomethyl trifluoromethylsulfonate (Tetrahedron Lett., 1986, 1477; 907 mg, 3.33 mmol) in methylene chloride (2 mL). The mixture is stirred at room temperature for 18 hours. Water (20 mL) and methylene chloride (20 mL) are added. The organic layer is separated, dried over anhydrous sodium sulfate, filtered and concentrated in vacuo. The residue is purified by flash-chromatography on silica gel, eluting with ethyl acetate to afford (S)-5-(biphenyl-4-yl)-4-[(dimethylphosphonomethyl)-amino]- 2-pentenoic acid ethyl ester as a pale yellow oil (Rf=0.3 in EtOAc).

(2) Similarly prepared is (S)-5-(biphenyl-4-yl)-4-(phosphonomethylamino)-pentanoic acid, m.p.: 213°–215°, $[\alpha]_D$=+2.87 (c 0.64, 0.1N NaOH).

The starting (S)-5-(biphenyl-4-yl)-4-[(dimethylphosphonomethyl)-amino]-pentanoic acid is prepared from (S)-4-(t-butoxycarbonylamino)-5-(biphenyl-4-yl)-pentanoic acid ethyl ester. Such is in turn prepared as follows: (S)-4-(t-Butoxycarbonylamino)-5-(biphenyl-4-yl)-pentenoic acid ethyl ester (1.6 g), is dissolved in ethanol and hydrogenated under 48 psi for 2 hours with Pd/C catalyst. The mixture is filtered through Celite and the filtrate is concentrated in vacuo to yield (S)-4-(t-butoxycarbonylamino)-5-(biphenyl-4-yl)-pentanoic acid ethyl ester.

EXAMPLE 15

(S)-3-(Biphenyl-4-yl)-2-[(diphenylphosphonomethyl)-amino]-propionic acid benzyl ester (0.8 g, 1.38 mmol) is dissolved in ethyl acetate (25 mL) and treated with hydrogen (50 lbs) in a Parr apparatus in the presence of 10% palladium on carbon (0.8 g). After uptake of 1 mole, the catalyst is filtered off and the solvent is evaporated in vacuo. The solid residue is recrystallized at 0° from ethyl acetate/hexane. After being dried under high vacuum at 50°, (S)-3-(biphenyl-4-yl)-2-[(diphenylphosphonomethyl)-amino]-propionic acid is obtained as a white solid, m.p. 118°–119°; $[\alpha]_{405}$= +9.49 (c 1.01, CHCl$_3$)

The starting material is prepared as follows:

(S)-2-(t-butoxycarbonylamino-3-(biphenyl-4-yl)-propionic acid methyl ester (4.1 g, 11.5 mmol) is dissolved at room temperature in methanolic 1N sodium hydroxide (60 mL). The solution is stirred for 3 hours. Ether (30 mL) and water (30 mL) are added. The aqueous layer is separated and acidified with concentrated hydrochloric acid, then extracted with ether (2×20 mL) and dried over anhydrous sodium sulfate. Evaporation of the solvent under reduced pressure gives (S)-2(-t-butoxycarbonylamino)-3-(biphenyl-4-yl)-propionic acid as a white solid, m.p. 122°–123°.

(S)-2-(t-Butoxycarbonylamino)-3-(biphenyl-4-yl)propionic acid (5 g, 14.6 mmol) is dissolved in methylene chloride (25 mL) under nitrogen and the solution is cooled to 0°. Benzyl alcohol (2 mL, 19 mmol) and 4-dimethylaminopyridine (0.1 g) are added, followed by a solution of dicyclohexylocarbodiimide (3.3 g, 16.1 mmol) in methylene chloride (15 mL). After stirring for 1 hour at 0° and 1 hour at room temperature, the reaction mixture is filtered and the filtrate concentrated in vacuo. The residue is redissolved in ether (100 mL), washed successively with water, 0.5M sodium dihydrogenophosphate, water, saturated sodium bicarbonate and water. The organic layer is dried over anhydrous sodium sulfate, filtered and concentrated under reduced pressure. (S)-2(-t-butoxycarbonylamino)- 3-(biphenyl-4-yl)-propionic acid benzyl ester is obtained as a white solid, $[\alpha]_D$=–3.33 (c 0.91, CHCl$_3$).

A stirred solution of (S)-2-(t-butoxycarbonylamino)-3-(biphenyl-4-yl)-propionic acid benzyl ester (3.95 g, 9.15 mmol) in ethyl acetate (40 mL) under nitrogen is cooled to 0° and treated with hydrochloric acid gas (4 g). A precipitate appears and the mixture is warmed to room temperature and stirred for 1 hour. Ether (25 mL) is added and the solid is filtered off and briefly dried under high vacuum for 1 hour. (S)-2-amino-3-(biphenyl-4-yl)-propionic acid benzyl ester hydrochloride is obtained as white solid, $[\alpha]_D$=–21.14 (c 0.92, MeOH).

To a stirred mixture of (S)-2-amino-3-(biphenyl-4-yl)-propionic acid benzyl ester hydrochloride (4.7 g, 12.8 mmol) in ethyl acetate (100 mL) and water (100 mL) at 5° is added sodium bicarbonate (1.13 g, 13.5 mmol). The solution is stirred for 5 minutes, then aqueous formaldehyde (37% aq., 1.25 mL, 16.6 mmol) is added. The mixture is allowed to warm slowly to room temperature while being stirred vigorously for 18 hours. The organic layer is separated and the aqueous layer extracted with ethyl acetate (50 mL). The combined organic phases are washed with water (50 mL), dried over anhydrous sodium sulfate, filtered and concentrated in vacuo. The resulting crude hexahydrotriazine intermediate is obtained as a white solid that is dried under high vacuum. Some of that material (0.75 g, 2.18 mmol) is dissolved in toluene (10 mL) and kept under nitrogen. Diphenyl phosphite (0.5 mL, 2.62 mmol) is added and the solution is warmed in a bath pre-heated to 70°. After 2 hours, the reaction mixture is allowed to cool to room temperature. After evaporation of the solvent under reduced pressure, the residue is purified by flash-chromatography on silica gel, eluting with a gradient of ethyl acetate (50% to 90%) in hexane. The product is recrystallized from ether/hexane, affording (S)-3-(biphenyl-4-yl)-2-[(diphenylphosphonomethyl)-amino]-propionic acid benzyl ester as a while solid, m.p. 85°–86°; $[\alpha]_D$=+8.40 (c 1.04, CHCl$_3$).

EXAMPLE 16

The following compounds are prepared using procedures similar to Example 15.

(1) (S)-3-(Biphenyl-4-yl)-2-{[di-(3-methyl-phenyl)-phosphonomethyl]-amino}-propionic acid, m.p. 74°–76°; $[\alpha]_D$=–3.15 (c 0.97, CHCl$_3$).

The starting di-(3-methylphenyl)phosphite is prepared as follows:

To a stirred solution of m-cresol (5.1 g, 47 mmol) in methylene chloride (5 mL) cooled to 0° under nitrogen is added methanol (0.97 mL, 24 mmol). Phosphorus trichloride (2 mL, 23 mmol) is then added dropwise over 20 minutes. The flask is vented to allow the hydrochloric acid formed to escape, then the mixture is allowed to warm up slowly to room temperature and stirred for 10 hours. The solvent is removed under reduced pressure and the residue is dried under high vacuum. Di-(3-methylphenyl)phosphite is characterized by H$^1$-NMR in CDCl$_3$ (P—H: 7.27 ppm, J=727.5 Hz) and used without further purification.

The diaryl phosphite starting materials for the compounds listed below are similarly prepared from the appropriate phenol.

(2) (S)-3-(Biphenyl-4-yl)-2-{[di-(3,5-dimethyl-phenyl)-phosphonomethyl]-amino}-propionic acid, m.p. 76°–78°; $[\alpha]_D$=+2.48 (c 0.99, CHCl$_3$).

(3) (S)-3-(Biphenyl-4-yl)-2-{[di-(3-methoxyphenyl)-phosphonomethyl]-amino}-propionic acid.

(4) (S)-3-(Biphenyl-4-yl)-2-{[di-(4-acetylaminophenyl)-phosphonomethyl]-amino}-propionic acid.

(5) (S)-3-(2-Methoxy-biphenyl-4-yl)-2-[(diphenylphosphonomethyl)-amino]-propionic acid.

(6) (S)-3-(2'-Methoxy-biphenyl-4-yl)-2-[(diphenylphosphonomethyl)-amino]-propionic acid.

(7) (S)-3-(3-Methoxy-biphenyl-4-yl)-2-[(diphenylphosphonomethyl)-amino]-propionic acid.

(8) (S)-3-(3'-Methoxy-biphenyl-4-yl)-2-[(diphenylphosphonomethyl)-amino]-propionic acid.

(9) (S)-4-(Biphenyl-4-yl)-3-[(diphenylphosphonomethyl)-amino]-butyric acid.

(10) (S)-5-(Biphenyl-4-yl)-4-[(diphenylphosphonomethyl)-amino]-pentanoic acid.

(11) (S)-5-Biphenyl-4-yl)-4-[diphenylphosphonomethyl)-amino]-pentanoic acid.

EXAMPLE 17

To a stirred solution of (S)-3-(biphenyl-4-yl)-2-[(diphenyl-phosphonomethyl)-amino]-propionic acid in THF is added 2N hydrochloric acid. The mixture is stirred at room temperature for 18 hours. Ethyl acetate and water are added. The organic phase is separated and washed successively with 1N hydrochloric acid, water and brine. After filtration, the organic layer is concentrated and the residue is purified by flash-chromatography on silica gel, eluting with 4% of methanol in methylene chloride to yield (S)-3-(biphenyl-4-yl)-2-{[(mono-phenyl-phosphonomethyl)-amino]-propionic acid.

EXAMPLE 18

The following compounds are prepared similarly to procedure in Example 17.
(1) (S)-3-(biphenyl-4-yl)-2-{[mono-(3,5-dimethylphenyl)-phosphonomethyl]-amino}-propionic acid.
(2) (S)-3-(Biphenyl-4-yl)-2-{[mono-(3-methylphenyl)-phosphonomethyl]-amino}-propionic acid.
(3) (S)-3-(Biphenyl-4-yl)-2-{[mono-(3-methoxyphenyl)-phosphonomethyl]-amino}-propionic acid.
(4) (S)-3-(Biphenyl-4-yl)-2-{[mono-(4-acetylamino-phenyl)-phosphonomethyl]-amino}-propionic acid.
(5) (S)-3-(2-Methoxy-biphenyl-4-yl)-2-[(mono-phenyl-phosphonomethyl)-amino]-propionic acid.
(6) (S)-3-(2'-Methoxy-biphenyl-4-yl)-2-[(mono-phenyl-phosphonomethyl)-amino]-propionic acid.
(7) (S)-3-(3-Methoxy-biphenyl-4-yl)-2-[(mono-phenyl-phosphonomethyl)-amino]-propionic acid.
(8) (S)-3-(3'-Methoxy-biphenyl-4-yl)-2-[(mono-phenyl-phosphonomethyl)-amino]-propionic acid.

EXAMPLE 19

(S)-3-Biphenyl-4-yl-2-{[di-(ethoxycarbonylmethyl)-phosphonomethyl]-amino}-propionic acid benzyl ester (0.18 g, 0.3 mmol) is dissolved in ethyl acetate (12 mL) and hydrogenated at 50 lbs pressure in a Parr apparatus in the presence of 10% palladium on carbon (0.1 g). After 6 hours, the reaction mixture is filtered and concentrated in vacuo. The resulting gummy solid is recrystallized from ether-hexane at 0°. (S)-3-(biphenyl- 4-yl)-2-{[di-(ethoxycarbonylmethyl)-phosphonomethyl]-amino}-propionic acid after being dried under high vacuum at 45°, is obtained as a crystalline solid, m.p. 85°–87°.

The starting material is prepared as follows:

To a stirred solution of ethyl glycolate (7.2 g, 69 mmol) in cold (ice bath) methylene chloride (8 mL) is added dropwise phosphorus trichloride (2 mL, 23 mmol). The solution is stirred at room temperature for 16 hours. The solution is concentrated under high vacuum and the obtained crude di-(ethoxycarbonylmethyl)phosphite is used directly.

Alternately, di-(ethoxycarbonylmethyl)phosphite can be prepared as follows:

To a stirred solution of dry phosphorous acid (1 g, 12.2 mmol) in anhydrous acetonitrile (10 mL) under nitrogen, is added, at 0°, diisopropylethylamine (4.25 mL), followed by ethyl bromoacetate (2.72 mL, 24.4 mmol). The mixture is allowed to warm slowly to room temperature and stirred for 18 hours. The solvent is removed under reduced pressure and the residue taken up in ethyl acetate. The solid material is filtered off and the filtrate is washed successively with cold 1N hydrochloric acid and water. The organic layer is dried over anhydrous magnesium sulfate, filtered and concentrated in vacuo. The residue is dried under high vacuum, yielding di-(ethoxycarbonylmethyl)phosphite as an amber oil characterized by $H^1$-NMR in $CDCl_3$ (P—H: 7.23 ppm, J=625 Hz).

The hexahydro-triazine intermediate described in example 15 (0.28 g, 0.82 mmol) is dissolved in toluene (3.5 mL) under nitrogen and treated with di-(ethoxycarbonylmethyl)phosphite (0.41 g, 1.61 mmol). The solution is heated to 70° for 4 hours. Ethyl acetate (10 mL) is added at room temperature and the organic layer is washed successively with water, 1N hydrochloric acid and water before being dried over anhydrous sodium sulfate, filtered and concentrated in vacuo. The residue is purified by flash chromatography on silica gel, eluting with a gradient of ethyl acetate (35% to 50%) in hexane to give (S)-3-(biphenyl-4-yl)-2-{[di-(ethoxycarbonylmethyl)-phosphonomethyl]-amino}-propionic acid benzyl ester as an oil (MS: M+1=598).

EXAMPLE 20

The following compounds are prepared using procedure similar to Example 19.
(1) (S)-3-(Biphenyl-4-yl)-2-{[di-(isopropyloxycarbonylmethyl)-phosphonomethyl]-amino}-propionic acid.
(2) (S)-3-(Biphenyl-4-yl)-2-{[di-(dimethylcarbamoylmethyl)ophosphonomethyl]-amino}-propionic acid.
(3) (S)-3-(Biphenyl-4-yl)-2-{[di-(2,2,2,-trichloroethyl)-phosphonomethyl]-amino}-propionic acid.
(4) (S)-3-(2-Methoxy-biphenyl-4-yl)-2-{[di-(ethoxycarbonylmethyl)-phosphonomethyl]-amino}-propionic acid.
(5) (S)-3-(2'-Methoxy-biphenyl-4-yl)-2-{[di-(ethoxycarbonylmethyl)-phosphonomethyl]-amino}-propionic acid.
(6) (S)-3-(3-Methoxy-biphenyl-4-yl)-2-{[di-(ethoxycarbonylmethyl)-phosphonomethyl]-amino}-propionic acid.
(7) (S)-3-(3'-Methoxy-biphenyl-4-yl)-2-{[di-(ethoxycarbonylmethyl)-phosphonomethyl]-amino}-propionic acid.
(8) (S)-4-(Biphenyl-4-yl)-3-{[di-(ethoxycarbonylmethyl)-phosphonomethyl]-amino}-butyric acid.
(9) (S)-5-(Biphenyl-4-yl)-4-{[di-(ethoxycarbonylmethyl)-phosphonomethyl]amino}-pentanoic acid.

EXAMPLE 21

The following compounds are prepared using procedures similar to Examples 1 to 10;
(1) (S)-[2-phenyl-1-(1H-tetrazol-5-yl)ethylamino]-methylphosphonic acid, m.p. 255°–256°, $[\alpha]_D$: +39.34° (c 0.65, 0,1 NaOH);
(2) (S)-[2-(4-isopropyloxyphenyl)-1-(1H-tetrazol-5-yl)ethylamino]-methylphosphonic acid, m.p. 229°–232°, $[\alpha]_D$: +31.73° (c 1.01, 0.1 NaOH);
(3) (S)-[2-phenyl-1-(1H-tetrazol-5-yl)-ethylamino]methylphosphonic acid diphenyl ester.

EXAMPLE 22

Preparation of 1,000 capsules each containing 25 mg of the active ingredient, as follows:

| | |
|---|---|
| (S)-[2-Biphenyl-4-yl-1-(1H-tetrazol-5-yl)-ethylamino]-methylphosphonic acid diphenyl ester | 25.00 g |
| Lactose | 192.00 g |
| Modified starch | 80.00 g |
| Magnesium stearate | 3.00 g |

Procedure:

All the powders are passed through a screen with openings of 0.6 mm. The drug substance is placed in a suitable mixer and mixed first with the magnesium stearate, then with the lactose and starch until homogenous. No. 2 hard gelatin capsules are filled with 300 mg of said mixture each, using a capsule filling machine.

Analogously capsules are prepared, containing about 10–100 mg of the other compounds disclosed and exemplified herein.

EXAMPLE 23

Preparation of 1,000 capsules each containing 50 mg of the active ingredient, as follows:

| | |
|---|---|
| (S)-3-(Biphenyl-4-yl)-2-[(diphenylphosphono-methyl)-amino]-propionic acid | 50.00 g |
| Lactose | 167.00 g |
| Modified starch | 80.00 g |
| Magnesium stearate | 3.00 g |

Procedure:

All the powders are passed through a screen with openings of 0.6 mm. The drug substance is placed in a suitable mixer and mixed first with the magnesium stearate, then with the lactose and starch until homogenous. No. 2 hard gelatin capsules are filled with 300 mg of said mixture each, using a capsule filling machine.

Analogously capsules are prepared, containing about 10–100 mg of the other compounds disclosed and exemplified herein.

What is claimed is:

1. A method of inhibiting the endogenous formation and of decreasing the level of endothelin in mammals which comprises administering to a mammal in need thereof an effective endothelin converting enzyme inhibiting amount of a compound of the formula (I)

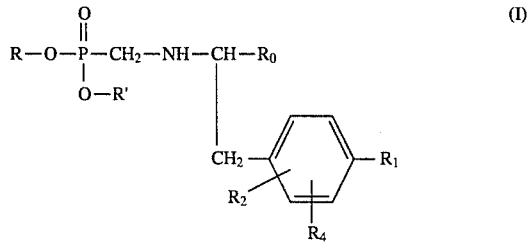

or a tautomer thereof, wherein
$R_0$ represents a group of formula

R and R' represent independently hydrogen, carbocyclic aryl, 6-tetrahydronaphthyl, 5-indanyl, α-(trichloromethyl, carboxyl, esterified carboxyl or amidated carboxyl) substituted-(lower alkyl or aryl-lower alkyl), acyloxymethyl optionally monosubstituted on methyl carbon by lower alkyl, by $C_5$–$C_7$-cycloalkyl, by aryl or by aryl-lower alkyl; $R_1$ represents phenyl, or phenyl substituted by lower alkyl, lower alkoxy, halogen or trifluoromethyl; or $R_1$ represents thienyl or furanyl optionally substituted by lower alkyl; or $R_1$ represents hydrogen if $R_0$ represents a group of formula Ia; $R_2$ and $R_4$ represent hydrogen, lower alkyl, hydroxy, lower alkoxy, halogen or trifluoromethyl; n is 0, 1 or 2; or a pharmaceutically acceptable salt thereof.

2. A method according to claim 1 wherein the compound is a compound of formula (III)

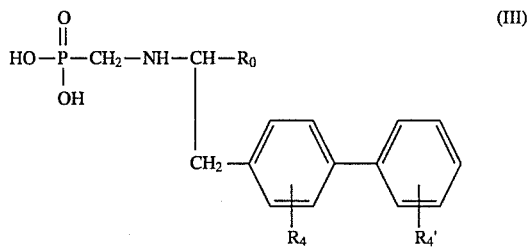

or a tautomer thereof, wherein $R_0$ represents a group of the formula (Ia); n is zero; $R_4$ and $R_4'$ represent hydrogen or $C_1$–$C_3$alkoxy; or a pharmaceutically acceptable mono- or di-ester derivative thereof in which one or two of the acidic hydroxy groups of the phosphono functional group are esterified in form of a mono- or di-pharmaceutically acceptable ester; or a pharmaceutically acceptable salt thereof; or an optical isomer thereof.

3. A method according to claim 2 wherein the compound is the (S)-enantiomer.

4. A method according to claim 2 wherein the compound is a compound of the formula IIIc, IIId, IIIe or IIIf

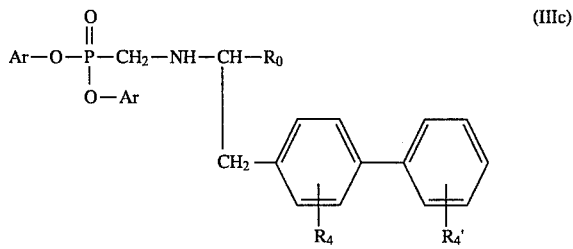

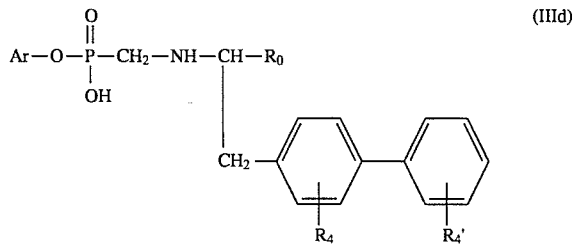

-continued

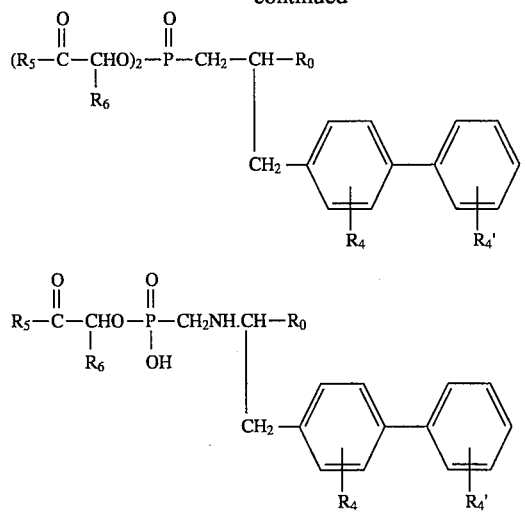

or a tautomer thereof wherein $R_0$ represents a group of the formula (Ia); n is zero; Ar represents phenyl or phenyl substituted by lower alkyl, lower alkoxy, halogen, trifluoromethyl, lower alkanoylamino, lower alkyl-(thio, sulfinyl or sulfonyl) or lower alkoxycarbonyl; or Ar represents 5-indanyl; $R_5$ represents hydroxy, lower alkoxy, aryl-lower alkoxy or di-lower alkylamino; $R_6$ represents hydrogen or lower alkyl; $R_4$ and $R_4'$ independently represent hydrogen or $C_1$–$C_3$alkoxy; or a pharmaceutically acceptable salt thereof.

5. A method according to claim 4 wherein the compound is a compound of formula IIIc or a tautomer thereof wherein $R_0$ represents a group of the formula (Ia); n is zero; Ar represents phenyl or phenyl substituted by $C_1$–$C_4$alkyl, by $C_1$–$C_4$alkoxy, by lower alkanoylamino, by carboxy-methyl, by lower alkoxycarbonyl-methyl, by N,N-di-lower alkylaminocarbonyl-methyl, or by trichloromethyl; $R_4$ and $R_4'$ independently represent hydrogen or $C_1$–$C_3$alkoxy; or a pharmaceutically acceptable salt thereof.

6. A method according to claim 1 wherein the compound is (S)-[2-(biphenyl)-4-yl-1-(tetrazol-5-yl)-ethylaminol-methylphosphonic acid or a pharmaceutically acceptable salt thereof; or a pharmaceutically acceptable pro-drug ester thereof.

7. A method according to claim 4 wherein the compound is (S)-[2-biphenyl-4-yl-1-(tetrazol-5-yl)-ethylamino]-methylphosphonic acid diphenyl ester.

8. A method according to claim 4 wherein the compound is (S)-[2-biphenyl-4-yl-1-(tetrazol-5-yl)-ethylamino]-methylphosphonic acid monophenyl ester.

9. A method of treating endothelin dependent disorders in mammals which comprises administering to a mammal in need thereof an effective endothelin converting enzyme inhibiting amount of a compound of the formula (I)

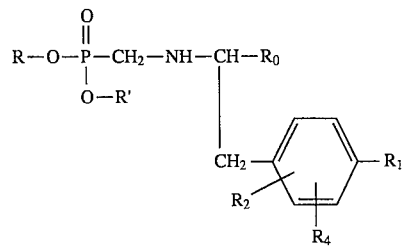

or a tautomer thereof wherein $R_0$ represents (i) a group of formula

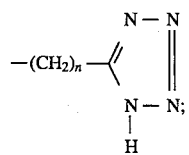

R and R' represent independently hydrogen, carbocyclic aryl, 6-tetrahydronaphthyl, 5-indanyl, α-(trichloromethyl, carboxyl, esterified carboxyl or amidated carboxyl) substituted-(lower alkyl or aryl-lower alkyl), acyloxymethyl optionally monosubstituted on methyl carbon by lower alkyl, by $C_5$–$C_7$-cycloalkyl, by aryl or by aryl-lower alkyl; $R_1$ represents phenyl, or phenyl substituted by lower alkyl, lower alkoxy, halogen or trifluoromethyl; or $R_1$ represents thienyl or furanyl optionally substituted by lower alkyl; or $R_1$ represents hydrogen if $R_0$ represents a group of formula Ia; $R_2$ and $R_4$ represent hydrogen, lower alkyl, hydroxy, lower alkoxy, halogen or trifluoromethyl; n is 0, 1 or 2; or a pharmaceutically acceptable salt thereof.

10. A method according to claim 9 wherein the compound is a compound of formula (III)

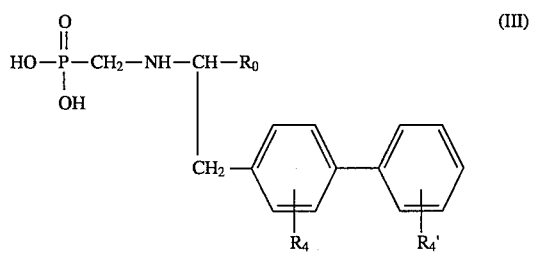

or a tautomer thereof, wherein $R_0$ represents a group of the formula (Ia); n is zero; $R_4$ and $R_4'$ represent hydrogen or $C_1$–$C_3$alkoxy; or a pharmaceutically acceptable mono- or di-ester derivative thereof in which one or two of the acidic hydroxy groups of the phosphono functional group are esterified in form of a mono- or di-pharmaceutically acceptable ester; or a pharmaceutically acceptable salt thereof; or an optical isomer thereof.

11. A method according to claim 10 wherein the compound is the (S)-enantiomer.

12. A method according to claim 10 wherein the compound is a compound of the formula IIIc, IIId, IIIe or IIIf

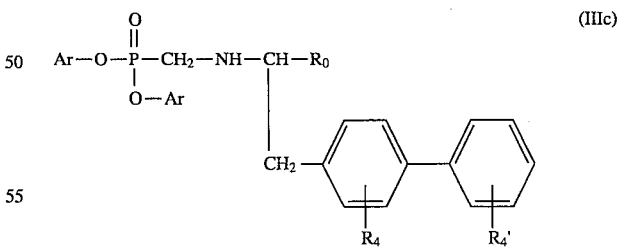

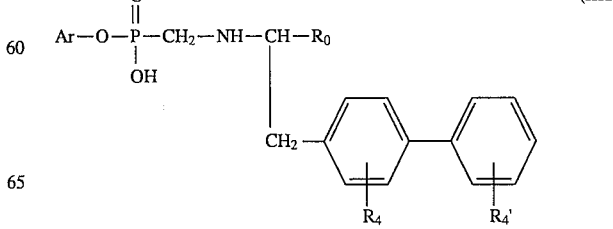

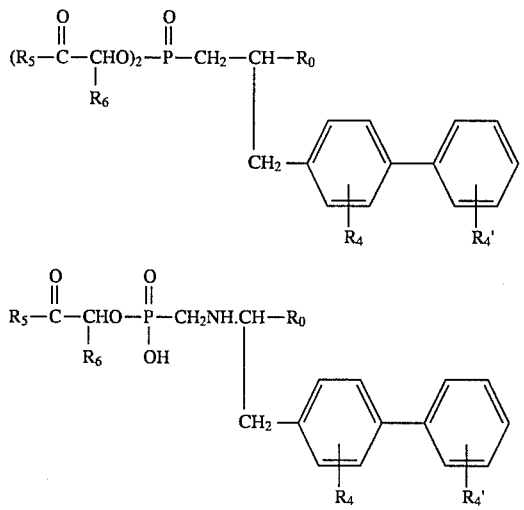

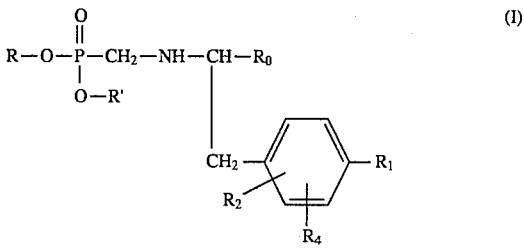

or a tautomer thereof wherein $R_0$ represents a group of the formula (Ia); n is zero; Ar represents phenyl or phenyl substituted by lower alkyl, lower alkoxy, halogen, trifluoromethyl, lower alkanoylamino, lower alkyl-(thio, sulfinyl or sulfonyl) or lower alkoxycarbonyl; or Ar represents 5-indanyl; $R_5$ represents hydroxy, lower alkoxy, aryl-lower alkoxy or di-lower alkylamino; $R_6$ represents hydrogen or lower alkyl; $R_4$ and $R_4'$ independently represent hydrogen or $C_1$–$C_3$alkoxy; or a pharmaceutically acceptable salt thereof.

13. A method according to claim 12 wherein the compound is a compound of formula IIIc or a tautomer thereof wherein $R_0$ represents a group of the formula (Ia); n is zero; Ar represents phenyl or phenyl substituted by $C_1$–$C_4$alkyl, by $C_1$–$C_4$alkoxy, by lower alkanoylamino, by carboxymethyl, by lower alkoxycarbonyl-methyl, by N,N-di-lower alkyl-aminocarbonyl-methyl, or by trichloromethyl; $R_4$ and $R_4'$ independently represent hydrogen or $C_1$–$C_3$alkoxy; or a pharmaceutically acceptable salt thereof.

14. A method according to claim 10 of treating cardiac or cerebral ischemia, or renal failure.

15. A method according to claim 14 of treating cerebral ischemia.

16. A method according to claim 14 wherein the compound is (S)-[2-(biphenyl)-4-yl-1-(tetrazol-5-yl)-ethylamino]-methylphosphonic acid or a pharmaceutically acceptable salt thereof; or a pharmaceutically acceptable pro-drug ester thereof.

17. A method according to claim 14 wherein the compound is (S)-[2-biphenyl-4-yl-1-(tetrazol-5-yl)-ethylamino]-methylphosphonic acid diphenyl ester.

18. A method according to claim 14 wherein the compound is (S)-[2-biphenyl-4-yl-1-(tetrazol-5-yl)-ethylamino]-methylphosphonic acid monophenyl ester.

19. An endothelin converting enzyme inhibiting pharmaceutical composition comprising an effective endothelin converting enzyme inhibiting amount of a compound of the formula (I)

or a tautomer thereof wherein $R_0$ represents a group of formula

R and R' represent independently hydrogen, carbocyclic aryl, 6-tetrahydronaphthyl, 5-indanyl, α-(trichloromethyl, carboxyl, esterified carboxyl or amidated carboxyl) substituted-(lower alkyl or aryl-lower alkyl), acyloxymethyl optionally monosubstituted on methyl carbon by lower alkyl, by $C_5$–$C_7$-cycloalkyl, by aryl or by aryl-lower alkyl; $R_1$ represents phenyl, or phenyl substituted by lower alkyl, lower alkoxy, halogen or trifluoromethyl; or $R_1$ represents thienyl or furanyl optionally substituted by lower alkyl; or $R_1$ represents hydrogen if $R_0$ represents a group of formula Ia; $R_2$ and $R_4$ represent hydrogen, lower alkyl, hydroxy, lower alkoxy, halogen or trifluoromethyl; n is 0, 1 or 2; or a pharmaceutically acceptable salt thereof.

20. A method according to claim 10 treating cerebral vasal spasm.

* * * * *